(12) United States Patent
Arad

(10) Patent No.: US 12,138,232 B2
(45) Date of Patent: Nov. 12, 2024

(54) COMPOUNDS FOR TREATING CORONAVIRUS INFECTION

(71) Applicant: NLC Pharma Ltd, Bnei-Brak (IL)

(72) Inventor: Dorit Arad, Tel Aviv (IL)

(73) Assignee: NLC Pharma Ltd, Bnei-Brak (IL)

( * ) Notice: Subject to any disclaimer, the term of this patent is extended or adjusted under 35 U.S.C. 154(b) by 0 days.

(21) Appl. No.: 18/393,798

(22) Filed: Dec. 22, 2023

(65) Prior Publication Data

US 2024/0130983 A1    Apr. 25, 2024

Related U.S. Application Data

(63) Continuation of application No. 17/887,461, filed on Aug. 14, 2022, now Pat. No. 11,857,517, which is a continuation of application No. PCT/IB2021/051256, filed on Feb. 15, 2021.

(60) Provisional application No. 62/976,420, filed on Feb. 14, 2020.

(51) Int. Cl.
```
A61K 31/122    (2006.01)
A61K 9/00      (2006.01)
A61K 9/127     (2006.01)
A61K 9/20      (2006.01)
A61K 9/28      (2006.01)
A61K 9/48      (2006.01)
A61K 31/198    (2006.01)
A61K 31/222    (2006.01)
A61K 31/381    (2006.01)
A61K 31/40     (2006.01)
A61K 31/422    (2006.01)
A61K 31/433    (2006.01)
A61K 31/454    (2006.01)
A61K 31/513    (2006.01)
A61K 31/536    (2006.01)
A61K 36/30     (2006.01)
A61P 31/14     (2006.01)
```

(52) U.S. Cl.
CPC .......... *A61K 31/122* (2013.01); *A61K 9/0053* (2013.01); *A61K 9/0095* (2013.01); *A61K 9/127* (2013.01); *A61K 9/2009* (2013.01); *A61K 9/2013* (2013.01); *A61K 9/2018* (2013.01); *A61K 9/2054* (2013.01); *A61K 9/2095* (2013.01); *A61K 9/282* (2013.01); *A61K 9/2833* (2013.01); *A61K 9/4833* (2013.01); *A61K 9/4858* (2013.01); *A61K 9/4866* (2013.01); *A61K 31/198* (2013.01); *A61K 31/222* (2013.01); *A61K 31/381* (2013.01); *A61K 31/40* (2013.01); *A61K 31/422* (2013.01); *A61K 31/433* (2013.01); *A61K 31/454* (2013.01); *A61K 31/513* (2013.01); *A61K 31/536* (2013.01); *A61K 36/30* (2013.01); *A61P 31/14* (2018.01); *A61K 2236/51* (2013.01)

(58) Field of Classification Search
CPC .................................................. A61K 31/122
USPC ............................................................ 514/681
See application file for complete search history.

(56) References Cited

U.S. PATENT DOCUMENTS

| | | | | |
|---|---|---|---|---|
| 2004/0198716 | A1* | 10/2004 | Arad | C07D 215/233 514/529 |
| 2005/0222258 | A1* | 10/2005 | Wang | A61K 31/22 514/549 |
| 2008/0182900 | A1* | 7/2008 | Wang | A61K 31/12 514/681 |
| 2022/0387354 | A1 | 12/2022 | Arad | |

FOREIGN PATENT DOCUMENTS

| | | | |
|---|---|---|---|
| CN | 109125252 A | 1/2019 | |
| WO | WO-2021161283 A1 * | 8/2021 | ........... A61K 31/122 |

OTHER PUBLICATIONS

International Search Report and the Written Opinion Dated Apr. 29, 2021 From the International Searching Authority Re. Application No. PCT/IB2021/051256. (21 Pages).

Notice of Allowance Dated Aug. 3, 2023 from the US Patent and Trademark Office Re. U.S. Appl. No. 17/887,461. (5 pages).

(Continued)

*Primary Examiner* — Raymond J Henley, III

(57) ABSTRACT

Described herein are compounds of Formula I:

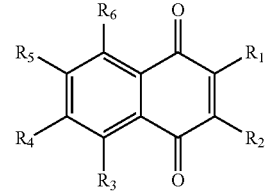

Formula I wherein $R_1$-$R_6$ are as described herein, for use in the treatment of a coronavirus infection; a method of inhibiting a coronavirus 3CL protease, by contacting the 3CL protease with a compound of Formula I; as well as methods pharmaceutical composition comprising a compound of Formula I and at least one phospholipid, wherein a weight ratio of the phospholipid(s) to the compound in the composition is in a range of from 10:1 to 1:10. Further described herein is a method of treating a coronavirus infection in a subject in need thereof, by administering to the subject at least one compound that exhibits at least two of: inhibition of an activity of a 3CL protease of the coronavirus; inhibition of inflammation in the subject; and inhibition of autophagy in the subject.

10 Claims, 5 Drawing Sheets

(56) References Cited

OTHER PUBLICATIONS

Notification of Office Action and Search Report Dated Mar. 1, 2024 From the State Intellectual Property Office of the People's Republic of China Re. Application No. 202180027955.4 and Its Machine Translation of Office Action Into English. (15 Pages).
Official Action Dated May 2, 2023 from the US Patent and Trademark Office Re. U.S. Appl. No. 17/887,461. (10 pages).
Restriction Official Action Dated Jan. 31, 2023 from the US Patent and Trademark Office Re. U.S. Appl. No. 17/887,461. (7 pages).
Supplementary European Search Report and the European Search Opinion Dated Feb. 12, 2024 From the European Patent Office Re. Application No. 21754154.9. (11 Pages).
Andujar et al. "Pharmacological Properties of Shikonin—A Review of Literature Since 2002", Planta Medica, 79(18): 1685-1697, Published Online Oct. 23, 2013.
Assimopoulou et al. "Preparative Isolation and Purification of Alkannin/Shikonin Derivatives From Natural Products by High-Speed Counter Current Chromatography", Biomedical Chromatography, 23(2): 182-198, Published Online Sep. 24, 2008.
Chen et al. "Cellular Pharmacology Studies of Shikonin Derivatives", Phytotherapy Research, 16(3): 199-209, May 2002.
Dai et al. "Structure-Based Design of Antiviral Drug Candidates Targeting the SARS-COV-2 Main Protease", Science, 368(6497): 1331-1335, Apr. 22, 2020.
Fan et al. "Anti-Inflammatory Effects of Shikonin in Human Periodontal Ligament Cells", Pharmaceutical Biology, 56(1): 415-421, Dec. 2018.
Guo et al. "Pharmacological Properties and Derivatives of Shikoninc—A Review in Recent Year", Pharmacological Research, 149: 104463, Published Online Sep. 22, 209.
Jo et al. "Characteristics of Flavonoids as Potent MERS-COV 3C-Like Protease Inhibition", Chemical Biology & Drug Design, 94(6): 2023-2030, Published Online Sep. 12, 2019.
Jo et al. "Inhibition of SARS-CoV 3CL Protease By Flavonoids", Journal of Enzyme Inhibition and Medicinal Chemistry,35(1): 145-151, Nov. 14, 2019.
Kontogiannopoulos et al. "Sterically Stabilized Liposomes As a Potent Carrier for Shikonin", Journal of Liposome Research, 24(3): 230-240, Mar. 6, 2014.
Li et al. "Biosynthesis of Novel Shikonin Glucosides by Enzymatic Glycosylation", Chemical and Pharmaceutical Bulletin, 67(10): 1072-1075, 2019.
Lin et al. "Anti-SARS Coronavirus 3C-Like Protease Effects of Isatis Indigotica Root and Plant-Derived Phenolic Compounds", Antiviral Research, 68(10): 36-42, Oct. 1, 2005.
Lu et al. "Phyto-Phospholipid Complexes (Phytosomes): A Novel Strategy to Improve the Bioavailability of Active Constituents", Asian Journal of Pharmaceutical Sciences, 14(3): 265-274, Available Online Jul. 27, 2018.
Lu et al. "Shikonin Extracted From Medicinal Chines Herbs Exters Anti-Inflammatory Effect Via Proteasome Inhibition", European Journal of Pharmacology, 658(2-3): 242-247, May 11, 2011.
Luo et al. "Anti-SARS Coronavirus 3C-Like Protease Effects of Rheum Palmatum L. Extracts", BioScience Trends, 3(4): 124-126, Aug. 2009.
Ma et al. "Ebsclen, Disulfiram, Carmofur, PX-12, Tideglusib, and Shikonin Arc Nonspecific Promiscuous SARS-CoV-2 Main Protease Inhibitors", ACS Pharmacology & Translational Science, 3(6): 1265-1277, XP055929280, Oct. 9, 2020.
Papageorgiou et al. "Alkannins and Shikonins: A New Class of Wound Healing Agents", Current Medicinal Chemistry, 15(30): 3248-3267, Dec. 2008.
Pillaiyar et al. "Middle East Respiratory Syndrome-Coronavirus (MERS-CoV): An Updated Overview and Pharmacotherapeutics", Medicinal Chemistry, 5(8): 361-372, Published Online Aug. 24, 2015.
Ramajayam et al. "Synthesis, Docking Studies, and Evaluation of Pyrimidines as Inhibitors of SARS-CoV 3CL Protease", Bioorganic & Medicinal Chemistry Letters, 20(12): 3569-3572, Available Online May 20, 2010.
Rao et al. "Proposing a Fungal Metabolite-Flaviolin as a Potential Inhibitor of 3CLpro of Novel Coronavirus SARS-CoV2 Using Docking and Molecular Dynamics", arXiv preprint arXiv:2004.03806:1-12, Apr. 8, 2020.
Ryu et al. "SARS-CoV 3CLpro Inhibitory Effects of Quinone-Methide Triterpenes from Tripterygium Regelii", Bioorganic & Medicinal Chemistry Letters, 20(6): 1873-1876, Mar. 15, 2010.
Shindo et al. "Shikonin Inhibits Inflammatory Cytokine Production in Human Periodontal Ligament Cells", Inflammation, 39(3): 1124-1129, Jun. 2016.
Xia et al. "Preparation, Cellular Uptake And Angiogenic Suppression Of Shikonin-Containing Liposomes In Vitro And In Vivo", Bioscience Report 33(2): e00020: 207-215, Feb. 1, 2013.
Xiong et al. "Shikonin Ameliorates Cerulein-Induced Acute Pancreatitis in Mice", Jorunal of Ethnopharmacology, 145(2): 573-580, Available Online Nov. 28, 2012.
Yang et al. "Drug Design Targeting the Main Protease, the Achilles' Heel of Coronaviruses", Current Pharmacology Design, 12(35): 4573-4590, Dec. 2006.
Zhao et al. "The Use of Response Surface Methodology to Optimize the Ultrasound-Assisted Extraction of Five Anthraquinones from *Rheum Palmatum* L.", Molecules, 16(7), 10.3390: 5928-5937, Jul. 15, 2011.
Zhu et al. "Identification of SARS-CoV-2 3CL Protease Inhibitors by a Quantitative High-Throughput Screening", ACS Pharmacology Translational Science. 3(5): 1008-1016, Sep. 3, 2020.
English Summary Date Jul. 9, 2024 from Notification of Office Action and Search Report Dated Mar. 1, 2024 From the State Intellectual Property Office of the People's Republic of China Re. Application No. 202180027955.4. (3 Pages).

* cited by examiner

COMPOUNDS FOR TREATING CORONAVIRUS INFECTION

RELATED APPLICATIONS

This application is a Continuation of U.S. patent application Ser. No. 17/887,461 filed on Aug. 14, 2022, which is a Continuation of PCT Patent Application No. PCT/IB2021/051256 having International Filing Date of Feb. 15, 2021, which claims the benefit of priority under 35 USC § 119(e) of U.S. Provisional Patent Application No. 62/976,420 filed on Feb. 14, 2020. The contents of the above applications are all incorporated by reference as if fully set forth herein in their entirety.

FIELD AND BACKGROUND OF THE INVENTION

The present invention, in some embodiments thereof, relates to therapy, and more particularly, but not exclusively, to compounds and compositions useful for treating coronavirus-associated diseases, such as COVID-19.

Coronaviruses are divided into alphacoronaviruses and betacoronaviruses (which infect mammals) and gammacoronaviruses and deltacoronaviruses (which primarily infect birds). The alphacoronaviruses include human coronaviruses 229E and NL63 (two of the many viruses associated with the common cold and other respiratory tract infections); whereas betacoronaviruses include human coronaviruses OC43 and HKU1 (additional viruses associated with the common cold and other respiratory tract infections), as well as Middle East respiratory syndrome-related coronavirus and Severe acute respiratory syndrome (SARS)-related coronaviruses such as SARS-CoV-1 (which is associated with the 2002-2004 SARS outbreak) and SARS-CoV-2 (which is associated with COVID-19).

Coronaviruses belong to the nidovirus order, part of the picornavirus-like supercluster, which includes picornaviruses, caliciviruses, and coronaviruses. These viruses possess a 3C protease (3Cpro) or 3C-like (3CL) protease (3CLpro), a cysteine protease which generally contains a typical chymotrypsin-like fold and a catalytic triad or dyad comprising a cysteine residue and a nucleophile. These proteases cleave the viral polyprotein, which is essential for viral replication. 3CLpro has been identified in several studies as an effective drug target for treating coronavirus infection [Yang et al., *Curr Pharm Des* 2006, 12:4573-4590]. The 3CLpro of the pandemic-causing SARS, MERS and 2019 Wuhan coronaviruses exhibits a high degree of conservation; for example, the homology between the 3CLpro of SARS and 2019 Wuhan coronavirus is 98%.

"Shikonin" refers to 5,8-dihydroxy-2-(1-hydroxy-4-methylpent-3-en-1-yl)naphthalene-1,4-dione; and more particularly to the (R)-enantiomer thereof, which is found in the roots of *Lithospermum erythrorhizon* (purple gromwell), a plant used in Chinese herbal medicine (in which it is referred to as "zicao") for treating a variety of inflammatory and infectious diseases. The (S)-enantiomer is known as "alkannin", a plant which has been used in folk medicine to treat abscesses and inflammations; and racemic mixtures are also known as "shikalkin".

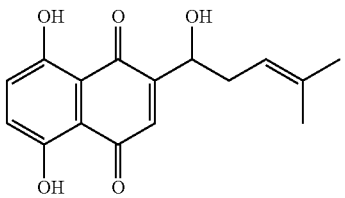

Shikonin

Shikonin has been reported to exhibit activities related to treatment of cancer, inflammation and wound healing [Guo et al., *Pharmacol Res* 2019, 149:104463]; as well as antiviral activity against HIV type I, adenovirus 3 (AdV3) and hepatitis C virus (HCV); and distinct anti-inflammation mechanisms, such as inhibition of leukotriene $B_4$ synthesis, suppression of mast cell degranulation, inhibition of neutrophil respiratory burst, alteration of phosphatidylinositol-mediated signaling, and blockade of chemokine binding to CCR-1 [Andujar et al., *Planta Med* 2013, 79:1685;] and reduction of interleukin-6, interleukin-8 and chemokine C-C motif ligand (CCL)20 production [Shindo et al., *Inflammation* 2016, 39:1124-1129].

U.S. Patent Application Publication No. 2004/0198716 describes quinones and quinone analogs, including shikonin and alkannin, useful for inhibiting cysteine proteases such as caspases and 3C cysteine proteases.

U.S. Patent Application Publication No. 2008/0182900 describes a use of compounds such as shikonin and alkannin in treating infections by a virus (such as hepatitis virus, influenza virus, herpes virus, HIV and SARS virus) or *mycoplasma*, and malignant tumors.

Jo et al. [*Chem Biol Drug Des* 2019, 94:2023-2030] describes inhibition of MERS coronavirus 3CLpro by herbacetin, isobavachalcone, quercetin 3-β-D-glucoside, and helichrysetin; and concludes that flavonol and chalcone are suitable scaffolds for binding with the catalytic site of MERS coronavirus 3CLpro.

Lu et al. [*Asian J Pharm Sci* 2019, 14:265-274] describes enhancement of absorption of active agents extracted from plants, by formation of complexes of the active agent with amphipathic phospholipids at defined molar ratios (described therein as "phyto-phospholipid complexes" or "phytosomes").

Coronaviruses further comprise a papain-like (PL) protease, which is responsible for cleaving the viral polyprotein at certain positions which are not cleaved by 3CL protease [Pillaiyar et al., *Med Chem* 2015, 5:361-372]. In addition, some coronaviruses use activation by TMPRSS2 (Transmembrane protease, serine 2), a human serine protease, to enter cells. Inhibitors of PL protease and TMPRSS2 have been proposed for antiviral use.

Drugs which have been used to treat coronavirus infection include chloroquine and hydroxychloroquine. These drugs have been reported to exhibit moderate antiviral activity against a wide variety of viruses, which may be associated with inhibition of autophagy, a natural cell process which many viruses use to promote their own replication.

Additional background art includes U.S. Patent Application Publication No. 2005/0222258; Assimopoulou et al. [*Biomed Chromatogr* 2009, 23:182-198]; Chen et al. [*Phytother Res* 2002, 16:199-209]; Dai et al. [*Science* 2020, 368:1331-1335]; Fan et al. [*Pharm Biol* 2018, 56:415-421]; Lu et al. [*Eur J Pharmacol* 2011, 658:242-247]; Papageorgiou et al. [*Curr Med Chem* 2008, 15:3248-3267]; Ramajayam et al. [*Bioorg Med Chem Lett* 2010, 20:3569-3572];

Xia et al. [*Biosci Rep* 2013, 33:e00020]; Xiong et al. [*J Ethnopharmacol* 2013, 145:573-580]; and Zhu et al. [*ACS Pharmacol Transl Sci* 2020, 3:1008-1016].

SUMMARY OF THE INVENTION

According to an aspect of some embodiments of the invention, there is provided a compound for use in the treatment of a coronavirus infection, the compound being represented by Formula I:

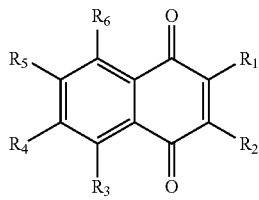

Formula I wherein $R_1$-$R_6$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, or alternatively, $R_1$ and $R_2$ together form a five- or six-membered aromatic or aliphatic ring.

According to an aspect of some embodiments of the invention, there is provided a pharmaceutical composition comprising:

a compound represented by Formula I:

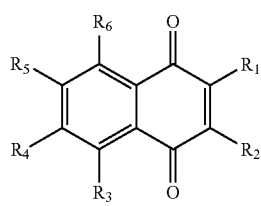

Formula I wherein $R_1$-$R_6$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, or alternatively, $R_1$ and $R_2$ together form a five- or six-membered aromatic or aliphatic ring; and at least one phospholipid, wherein a weight ratio of the at least one phospholipid to the compound in the composition is in a range of from 10:1 to 1:10.

According to an aspect of some embodiments of the invention, there is provided a method of inhibiting a coronavirus 3CL protease, the method comprising contacting the 3CL protease with a compound represented by Formula I:

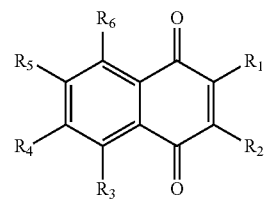

Formula I wherein $R_1$-$R_6$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, or alternatively, $R_1$ and $R_2$ together form a five- or six-membered aromatic or aliphatic ring.

According to an aspect of some embodiments of the invention, there is provided a method of treating a coronavirus infection in a subject in need thereof, the method comprising administering to the subject at least one compound that exhibits at least two of:

(i) inhibition of an activity of a 3CL protease of the coronavirus;

(ii) inhibition of inflammation in the subject; and (iii) inhibition of autophagy in the subject, thereby treating the coronavirus infection.

According to some embodiments of any of the embodiments relating to a method of treating a coronavirus infection by administering a compound, the compound is represented by Formula I:

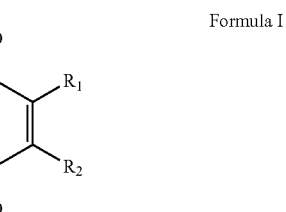

Formula I wherein $R_1$-$R_6$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, or alternatively, $R_1$ and $R_2$ together form a five- or six-membered aromatic or aliphatic ring.

According to some embodiments of any of the embodiments relating to Formula I, at least one of $R_3$ and $R_6$ is OH.

According to some embodiments of any of the embodiments relating to Formula I, $R_3$ and $R_6$ are each OH.

According to some embodiments of any of the embodiments relating to Formula I, $R_2$, $R_4$ and $R_5$ are hydrogen.

According to some embodiments of any of the embodiments relating to Formula I, $R_1$ is represented by:

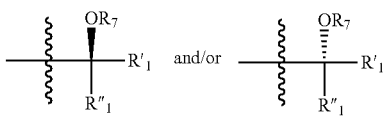

wherein $R'_1$, $R''_1$, and $R_7$ are each independently selected from the group consisting of hydrogen, alkyl, alkenyl, alkynyl, cycloalkyl, heteroalicyclic, and carbonyl.

According to some embodiments of any of the respective embodiments, $R'_1$ is alkenyl.

According to some embodiments of any of the respective embodiments, $R'_1$ is —$CH_2$—$CH$=$C(CH_3)_2$.

According to some embodiments of any of the respective embodiments, $R_7$ is a saccharide moiety (e.g., glycosyl) or a peptide moiety.

According to some embodiments of any of the respective embodiments, $R_7$ is hydrogen or carbonyl.

According to some embodiments of any of the embodiments described herein relating to a compound, the compound is shikonin or a glycoside of shikonin, or an ester thereof.

According to some embodiments of any of the embodiments described herein relating to a compound or a method utilizing the compound, the compound is part of a composition which further comprises one or more phospholipid(s), and a weight ratio of the phospholipid(s) to the compound in the composition is in a range of from 10:1 to 1:10.

According to some embodiments of any of the embodiments described herein relating to a compound or a method utilizing the compound, the compound is part of a composition which further comprises liposomes.

According to some embodiments of any of the embodiments described herein relating to a composition, the composition further comprising liposomes.

According to some embodiments of any of the embodiments described herein relating to a composition, the composition further comprises at least one additional active agent selected from the group consisting of a vitamin, N-acetyl cysteine, an anticoagulant, an anti-inflammatory agent, an antipyretic agent, an antiviral agent, and a protease inhibitor.

According to some embodiments of any of the embodiments described herein relating to a composition, the composition is for use in the treatment of a coronavirus infection.

According to some embodiments of any of the embodiments described herein relating to a method of inhibiting a coronavirus 3CL protease, the method comprises administering a compound described herein to a subject in need thereof.

According to some embodiments of any of the embodiments described herein relating to a treatment, the treatment is of a subject in which inhibiting inflammation would be beneficial.

According to some embodiments of any of the embodiments described herein relating to a treatment or method of inhibiting a coronavirus 3CL protease, the treatment or method comprises administration of the compound from 2 to 6 times per day.

According to some embodiments of any of the embodiments described herein relating to a treatment or a method of inhibiting a coronavirus 3CL protease, the treatment or method comprises intravenous administration of the compound.

According to some embodiments of any of the embodiments described herein relating to a treatment or a method of inhibiting a coronavirus 3CL protease, the treatment or method comprises administering the compound at a dose in a range of from 0.04 mg to 400 mg.

According to some embodiments of any of the embodiments described herein relating to a treatment or a method of inhibiting a coronavirus 3CL protease, the treatment or method comprises oral administration of the compound.

According to some embodiments of any of the embodiments described herein relating to a treatment or a method of inhibiting a coronavirus 3CL protease, the treatment or method comprises administering the compound at a dose in a range of from 10 mg to 5 grams.

According to some embodiments of any of the embodiments described herein relating to a treatment or a method of inhibiting a coronavirus 3CL protease, the treatment or method comprises administering the compound at a dosage in a range of from 2 mg per kg per day to 200 mg per kg per day.

According to some embodiments of any of the embodiments described herein relating to a treatment or a method of inhibiting a coronavirus 3CL protease, the treatment or method comprises administering at least one additional active agent selected from the group consisting of a vitamin, N-acetyl cysteine, an anticoagulant, an anti-inflammatory agent, an antipyretic agent, an antiviral agent, and a protease inhibitor.

According to some embodiments of any of the respective embodiments described herein, a dosage of N-acetyl cysteine is in a range of from 0.2 to 6.4 grams per day.

According to some embodiments of any of the embodiments described herein relating to an additional active agent which is a protease inhibitor, the protease inhibitor is capable of inhibiting 3C protease and/or a 3CL protease.

According to some embodiments of any of the embodiments described herein relating to a treatment or a method of inhibiting a coronavirus 3CL protease, the treatment or method comprises administering the at least one additional active agent 4 times per day.

According to some embodiments of any of the embodiments described herein relating to a treatment or a method of inhibiting a coronavirus 3CL protease, the treatment or method further comprises inhibiting inflammation and/or autophagy in the subject.

According to some embodiments of any of the embodiments relating to a method of treating a coronavirus infection, the method comprises administering to the subject a compound capable of at least two of inhibition of activity of 3CL protease, inhibition of inflammation, and inhibition of autophagy.

According to some embodiments of any of the embodiments relating to a method of treating a coronavirus infection, the compound is capable of each of inhibition of activity of 3CL protease, inhibition of inflammation, and inhibition of autophagy.

According to some embodiments of any of the embodiments relating to a method of treating a coronavirus infection, the method comprises administering to the subject the compound of Formula I (according to any of the respective embodiments described herein) and at least one additional agent that exhibits inhibition of activity of 3CL protease, inhibition of inflammation, and/or inhibition of autophagy.

According to some embodiments of any of the embodiments described herein relating to a coronavirus, the coronavirus is a betacoronavirus.

According to some embodiments of any of the embodiments described herein relating to a coronavirus, the coronavirus is a SARS-related coronavirus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
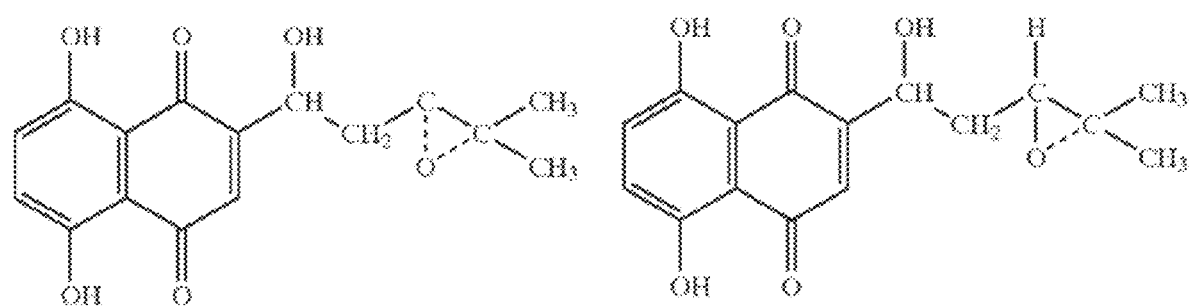
FIGS. 1A and 1B present exemplary naphthoquinone compounds according to some embodiments of the invention.

The present invention, in some embodiments thereof, relates to therapy, and more particularly, but not exclusively, to compounds and compositions useful for treating coronavirus-associated diseases, such as COVID-19.

Before explaining at least one embodiment of the invention in detail, it is to be understood that the invention is not necessarily limited in its application to the details set forth in the following description or exemplified by the Examples.

The invention is capable of other embodiments or of being practiced or carried out in various ways.

In a search for treatments of coronavirus infection with an acceptable level of side effects, the present inventor has uncovered a class of naphthoquinone compound, including many naturally occurring compounds, which exhibit a surprising ability to treat coronavirus infections, for example, by exhibiting an antiviral effect and/or an anti-inflammatory effect.

While reducing the present invention to practice, the present inventor has shown the efficacy of shikonin at inhibiting 3CL protease of SARS-coronavirus 2, and the ability of plant extracts containing shikonin derivatives to treat SARS-coronavirus 2 infection.

As shown in the Examples section herein, exemplary compositions comprising purple gromwell extract, known to contain shikonin or derivatives thereof, reduced mortality, signs of inflammation and other disease symptoms in patients afflicted by COVID-19, relative to a control treatment. As further shown therein, such compositions exhibited inhibition of viral 3CL protease.

Thus, according to an aspect of some embodiments of the invention there is provided a compound, as described herein, which may useful in the treatment of a viral infection, for example, a coronavirus infection.

Compound:

The compound according to some of any of the respective embodiments described herein is represented by Formula I:

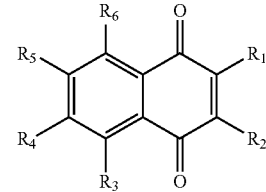

Formula I wherein $R_1$-$R_6$ are each independently hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and/or amino, or alternatively, $R_1$ and $R_2$ together form a five- or six-membered aromatic or aliphatic ring.

For the sake of brevity, a compound according to Formula I is referred to herein interchangeably as a "naphthoquinone compound".

In some of any of the respective embodiments described herein, at least one of $R_3$ and $R_6$ is OH. In some such embodiments, $R_3$ and $R_6$ are each OH. In some embodiments, $R_3$ and $R_6$ are each OH and $R_2$, $R_4$ and $R_5$ are each hydrogen.

Alternatively, at least one of $R_3$ and $R_6$ (and optionally both $R_3$ and $R_6$) is a functional group derived from OH (rather than OH), such as O-carboxy or a saccharide moiety (which may form OH upon cleavage of the ester bond).

In some of any of the respective embodiments described herein, each of $R_3$-$R_6$ is each independently OH (or a functional group derived from OH) or hydrogen.

In some of any of the respective embodiments described herein, $R_2$, $R_4$ and $R_5$ are each hydrogen.

Figure 1B:
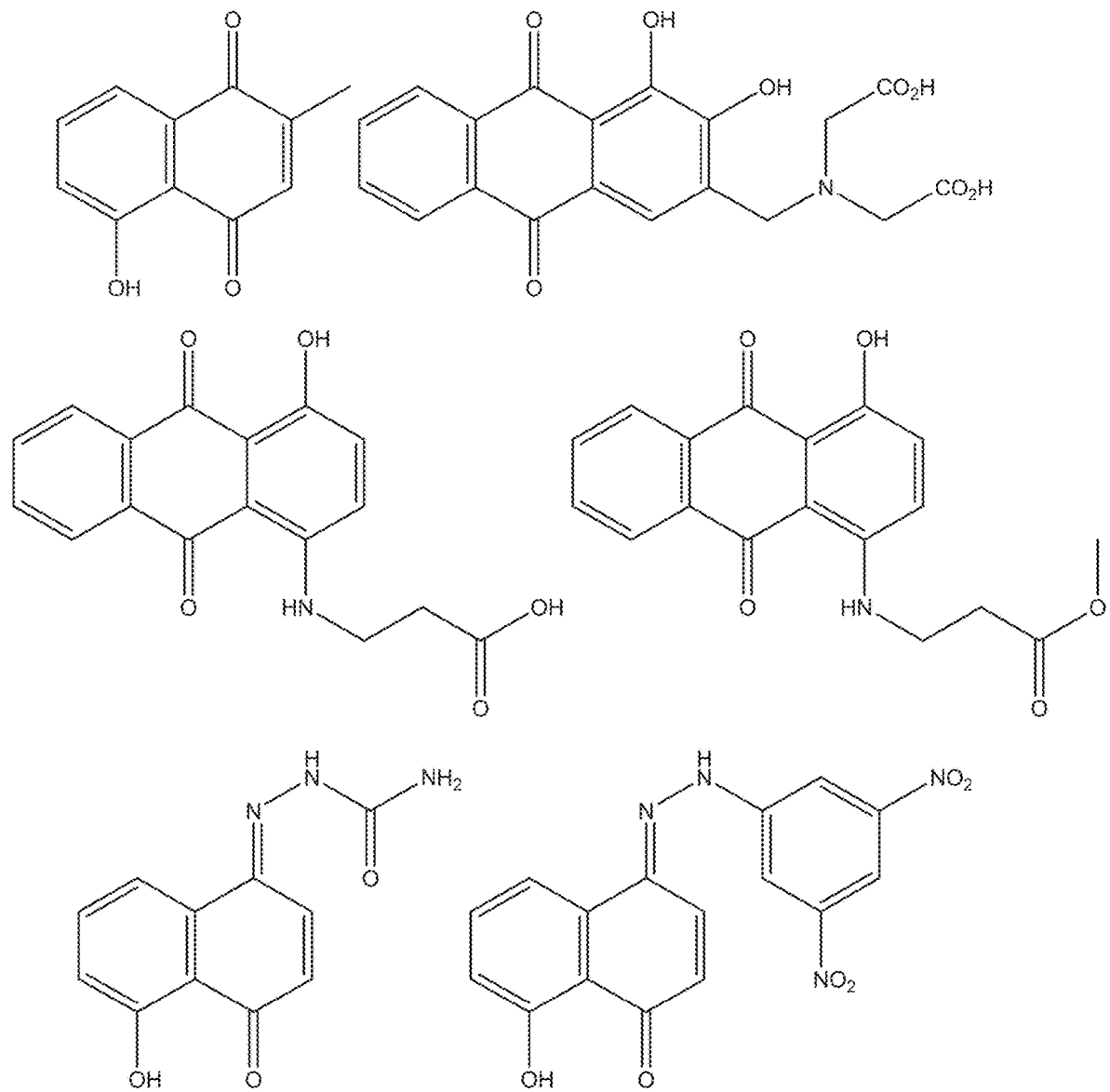
Figure 2:
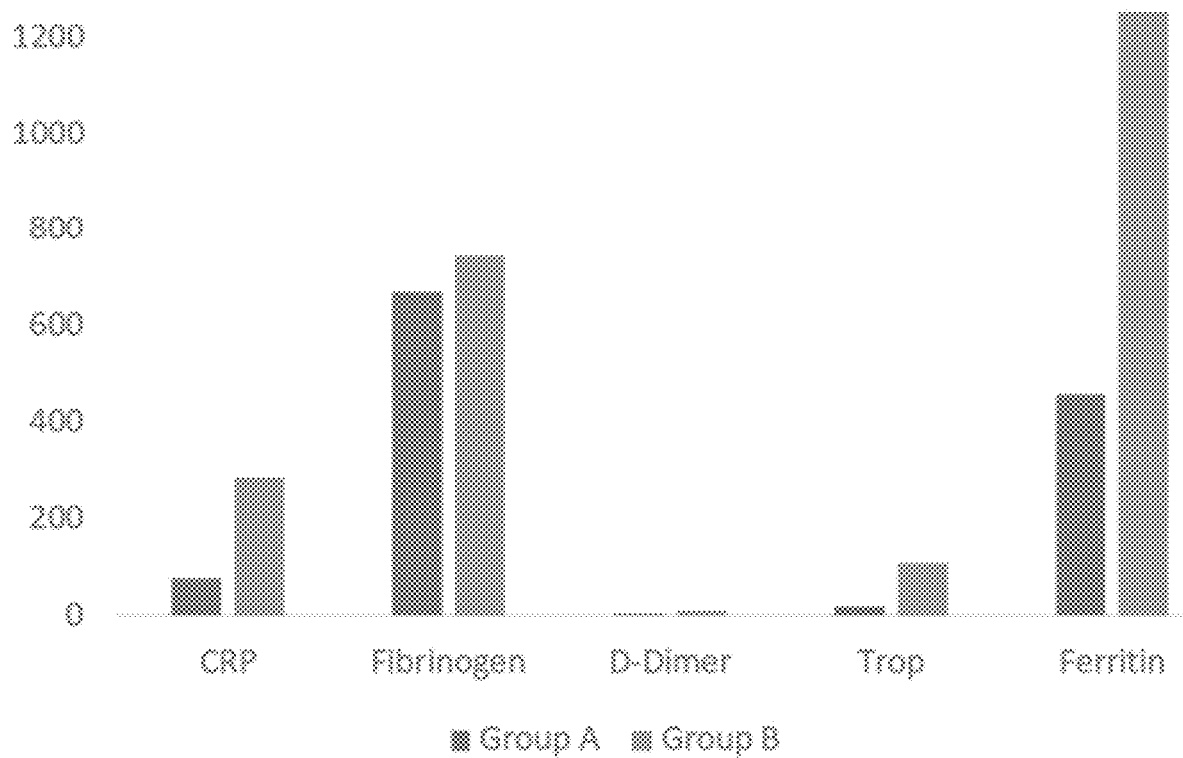
FIG. 2 presents a bar graph showing the average of the maximal values of levels of CRP, fibrinogen, D-dimer, troponin (trop) and ferritin in COVID-19 patients treated with an composition comprising purple gromwell extract (Group A) or with vitamin C and *spirulina* dietary supplement (Group B); Group A included 10 patients and Group B included 19 patients.

In embodiments, wherein $R_1$ and $R_2$ together form a five- or six-membered aromatic or aliphatic ring, the ring may be unsubstituted or substituted, e.g., by any substituent described herein for a cycloalkyl, heteroalicyclic, aryl or heteroaryl. In some such embodiments, the ring is an aromatic carbon ring, such that the compound is a substituted or unsubstituted 9,10-anthroquinone. Exemplary 9,10-anthroquinones are depicted in FIG. 1B.

In some of any of the respective embodiments described herein, $R_1$ is a substituted or unsubstituted alkyl or alkenyl. In some such embodiments, $R_2$ is hydrogen.

In some of any of the respective embodiments described herein, $R_1$ is represented by:

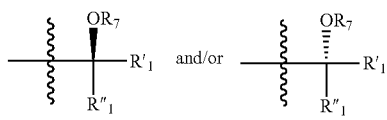

wherein $R'_1$, $R''_1$, and $R_7$ are each independently selected from the group consisting of hydrogen, alkyl, alkenyl, alkynyl, cycloalkyl, heteroalicyclic, and carbonyl. By "and/or" it is meant that the compound may comprise one stereoisomer or the other, or a racemic mixture in which both stereoisomer are present in approximately equal proportions, or a mixture enriched with stereoisomer relative to the other.

In some of any of the respective embodiments described herein, $R'_1$ is alkenyl, for example, —$CH_2$—CH=C($CH_3$)$_2$.

In some of any of the respective embodiments described herein, $R''_1$ is hydrogen.

In some of any of the respective embodiments described herein, $R_7$ is hydrogen (e.g., as in shikonin) or a carbonyl group (e.g., as in an ester of shikonin), such as acetyl (—C(=O)$CH_3$), propionyl (—C(=O)$CH_2CH_3$), isobutyryl ((—C(=O)CH($CH_3$)$_2$), isovaleryl (—C(=O)$CH_2$CH($CH_3$)$_2$), O-hydroxyisovaleryl (—C(=O)$CH_2$C(OH)($CH_3$)$_2$), α-methyl-n-butyryl (—C(=O)CH($CH_3$)$CH_2CH_3$), α,β-dimethylacryl ((—C(=O)C($CH_3$)=CHCH$_3$) and/or β,β-dimethylacryl ((—C(=O)CH=C($CH_3$)$_2$).

Shikonin is an exemplary compound according to embodiments of the invention (wherein $R_3$ and $R_6$ are OH, $R_2$, $R_4$ and $R_5$ are hydrogen, and $R_1$ is —CH(OH)—CH=C($CH_3$)$_2$).

In some of any of the respective embodiments described herein, $R_1$ is —$CH_2CH_2$CH=C($CH_3$)$_2$, for example, in deoxyshikonin (wherein $R_3$ and $R_6$ are OH, and $R_2$, $R_4$ and $R_5$ are hydrogen).

Shikonin (or any other naphthoquinone compound described herein) may also be in a form of a glycoside of shikonin, for example, wherein one or more OH of shikonin is replaced by a saccharide moiety (e.g., in a form of a substituted alkoxy group); and/or an ester of shikonin (or a glycoside of shikonin), for example, wherein one or more OH of shikonin (or a glycoside of shikonin) is replaced by a O-carboxy group (e.g., —O—C(=O)$CH_3$).

The term "glycosyl", as used herein, refers to a chemical group which is obtained by removing the hydroxyl group from the hemiacetal function of a monosaccharide and, by extension, of a lower oligosaccharide (e.g., a disaccharide, a trisaccharide, etc.).

The term "glycoside", as used herein, refers to a compound which comprises one or more glycosyl group (as defined herein). For example, a "shikonin glycoside" refers to shikonin attached to one or more glycosyl group.

As used herein, the term "saccharide moiety" describes a moiety, as defined herein, that contains one or more saccharide units.

As used herein the term "moiety" describes a major portion of a first molecule which is covalently linked to another molecule and which retains its main structural features and/or activity. Thus, a "moiety" refers to a part of a molecule formed by conjugating the aforementioned first molecule to one or more other molecules, and represents that portion of the first molecule that is present in the conjugation product. For example, a saccharide moiety may comprise all of a saccharide except for one hydroxyl group (e.g., as described hereinabove with respect to glycosyl).

Accordingly, a "saccharide moiety" is that portion of a saccharide molecule formed upon conjugating a second molecule (e.g., a naphthoquinone compound) thereto.

In exemplary embodiments of the invention, the saccharide moiety contains one saccharide unit and the saccharide unit is a monosaccharide.

The term "monosaccharide", as used herein and is well known in the art, refers to a simple form of a sugar that consists of a single saccharide unit which cannot be further decomposed to smaller saccharide building blocks or moieties. Common examples of monosaccharides include glucose (dextrose), fructose, galactose, mannose, and ribose. Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms. Monosaccharides are the building blocks of oligosaccharides like sucrose (common sugar) and other polysaccharides (such as cellulose and starch).

The above monosaccharides encompass both D- and L-monosaccharides.

Alternatively, the monosaccharide can be a monosaccharide derivative, in which the saccharide unit comprises one or more substituents other than hydroxyls. Such derivatives can be, but are not limited to, ethers, esters, amides, acids, phosphates and amines. Amine derivatives include, for example, glucosamine, galactosamine, fructosamine and mannosamine. Amide derivatives include, for example, N-acetylated amine derivatives of saccharides (e.g., N-acetylglucosamine, N-acetylgalactosamine).

The term "oligosaccharide" as used herein refers to a compound or moiety that comprises two or more linked monosaccharide units, as these are defined herein. According to some embodiments of the present invention, an oligosaccharide comprises 2-6 monosaccharides. Alternatively, an oligosaccharide comprises 2-4 monosaccharides, or further alternatively, an oligosaccharide is a disaccharide moiety, having two monosaccharide units.

The term "disaccharide" as used herein refers to a compound or moiety that comprises two linked monosaccharide units.

The term "trisaccharide" as used herein refers to a compound or moiety that comprises three linked monosaccharide units.

Non-limiting examples of shikonin glycosides (e.g., shikonin-1,8-di-O-β-D-glucopyranoside and shikonin-1'-O-β-D-glucopyranoside), and techniques which may optionally be used to prepare them, are presented in Li et al. [*Chem Pharm Bull* (Tokyo) 2019, 67:1072-1075] and Su et al. [*Eur J Med Chem* 2010, 45:2713-2718], each of which is incorporated herein by reference in its entirety, especially with respect to the species of glycosides described therein.

A glycoside according to any of the respective embodiments described herein may optionally comprise one or more (e.g., 1, 2 or 3) monosaccharide moieties (e.g., a glucose moiety, a galactose moiety, and/or a rhamnose moiety), one or more disaccharide moieties (e.g., a glucosyl-(1→2)-glucosyl and/or a rutinose moiety), and/or one or more trisaccharide moieties (e.g., a glucosyl-(1→2)-glucosyl-(1→2)-glucosyl and/or a 2$^G$-rhamnosylrutinose moiety).

The compounds and structures described herein encompass any stereoisomer, including enantiomers and diastereomers, of the compounds described herein, unless a particular stereoisomer is specifically indicated.

Thus, for example, the term "shikonin" herein encompasses both the (R) and (S) enantiomers of 5,8-dihydroxy-2-(1-hydroxy-4-methylpent-3-en-1-yl)naphthalene-1,4-dione, unless a specific enantiomer is indicated. For example, the term "alkannin" refers herein specifically to the (S) enantiomer.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an (R) or an (S) configuration and any combination, and compounds according to some embodiments of the present invention, can have any their chiral centers exhibit an (R) or an (S) configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

Imines and hydrazones of naphthoquinone compounds described herein, e.g., wherein one or more of the oxo (═O) groups of a compound of Formula I is replaced by an ═N—R' (imine) or ═N—NR'R" (hydrazone), wherein R' and R" are as described herein, are encompassed by the invention. Examples of such compounds include hydrazones formed from 5-hydroxyquinone and hydrazine carboxamide or 3,5-dinitrophenylhydrazine, as depicted in FIG. 1B.

In some of any of the respective embodiments, $R_3$ or $R_4$ or $R_5$ or $R_6$ is a naphthoquinone moiety which is also represented by Formula I, for example, such that the compound may be regarded as a dimer of a compound wherein $R_3$ or $R_4$ or $R_5$ or $R_6$ is hydrogen (or, if the aforementioned naphthoquinone moiety is likewise attached another naphthoquinone moiety, as a trimer or longer oligomer of such a compound). In some such embodiments, $R_3$ and $R_6$ are hydroxy, and $R_4$ or $R_5$ is the aforementioned naphthoquinone moiety.

Oligomerization of shikonin (including alkannin) is discussed in more detail in Assimopoulou et al. [*Biomed Chromatogr* 2009, 23:182-198], the contents of which are incorporated herein by reference (especially with respect to the alkannin/shikonin-derived compounds described therein).

In some such embodiments, the naphthoquinone moiety is a substituted aryl, e.g., such that compound comprises two naphthoquinones according to Formula I which are attached to one another, wherein each naphthoquinones may be regarded as an $R_4$ or $R_5$ substituent of the other. An example of such a compound is presented below (in which either of the two naphthoquinone moieties may be regarded as an $R_4$ substituent of the other naphthoquinone moiety).

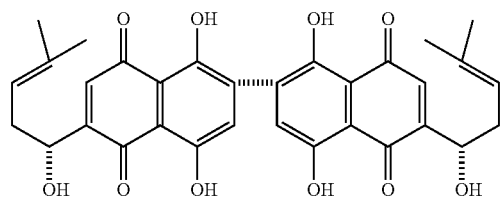

In some such embodiments, the naphthoquinone moiety is a substituted alkyl, e.g., an alkyl corresponding to $R_1$ according to any of the respective embodiments described herein, wherein the alkyl is substituted by a naphthoquinone moiety. In some such embodiments, a hydroxy group comprised by the $R_1$ (according to any of the respective embodiments described herein) is replaced by a covalent bond attaching the two naphthoquinone moieties. An example of such a compound is presented below (in which the naphthoquinone moiety on the left represents an $R_4$ substituent of the naphthoquinone moiety on the right).

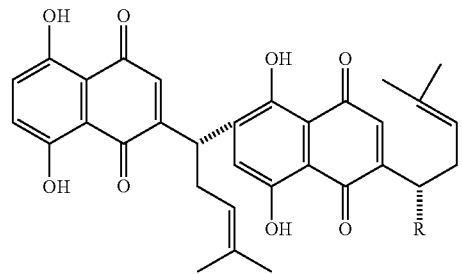

As will be readily apparent to the skilled person, trimers and longer oligomers may be formed by essentially the same types of linkage exemplified in the dimers hereinabove, and/or using naphthoquinone compounds other than shikonin as monomeric units (e.g., any compound according to Formula I may optionally serve as a monomeric unit).

In some of any of the respective embodiments, the composition comprises a compound having a molecular weight of about 420 to about 260 Da and/or a compound having a molecular weight of about 810 to about 850 Da. In some such embodiments, the aforementioned compound(s) is a shikonin derivative, e.g., shikonin substituted by a saccharide moiety (e.g., a monosaccharide moiety which results in a molecular weight of about 453 Da, or a trisaccharide moiety which results in a molecular weight of about 828 Da) or a shikonin trimer.

Exemplary naphthoquinone compounds include, without limitation, plumbagin (5-hydroxy-2-methyl-1,4-naphthoquinone), shikonin, acetyl shikonin, propionyl shikonin, isobutyryl shikonin, isovaleryl shikonin, β-hydroxyisovaleryl shikonin, α-methyl-n-butyryl shikonin, α,β-dimethylacryl shikonin, β,β-dimethylacryl shikonin, shikonin-1'-O-galactopyranoside, shikonin-1'-O-rhamnopyranoside, shikonin-1'-O-glucopyranoside, shikonin-1',8-di-O-glucopyranoside, 1',5,8-tri-O-glucopyranoside, shikonin-1'-O-glucosyl-(1→2)-glucopyranoside, shikonin-1'-O-glucosyl-(1→2)-glucosyl-(1→2)-glucopyranoside, shikonin-1'-O-rutinoside, shikonin-1'-O-2$^G$-rhamnosylrutinoside, and any dimer or trimer of shikonin described in Assimopoulou et al. [*Biomed Chromatogr* 2009, 23:182-198], including all stereoisomers thereof.

Further examples of naphthoquinone compounds include, without limitation:
a) compounds of Formula I, in which $R_3$ and $R_6$ are each OH and $R_2$, $R_4$ and $R_5$ are each hydrogen, and:
   $R_1$ is —CH=C(CH$_3$)$_2$;
   $R_1$ is —CH$_2$CH=C(CH$_3$)$_2$;
   $R_1$ is —C(=O)CH$_2$C=C(CH$_3$)$_2$;
   $R_1$ is —C(=NOH)CH$_2$C=C(CH$_3$)$_2$;
   $R_1$ is —C(=N—NH$_2$)CH$_2$C=C(CH$_3$)$_2$;
   $R_1$ is —C(=NH)CH$_2$C=C(CH$_3$)$_2$;
   $R_1$ is —CH(CO$_2$R)CH$_2$C=C(CH$_3$)$_2$(wherein R is hydrogen, alkyl, alkenyl, alkynyl, cycloalkyl, heteroalicyclic, aryl, or heteroaryl);
   $R_1$ is —CH(OH)CH$_2$CH$_2$CH(CH$_3$)$_2$;
   $R_1$ is —CH(OH)CH$_2$CH(OH)C(CH$_3$)$_2$OH;
   $R_1$ is —CH(OH)CH$_2$CH(OH)CH(CH$_3$)$_2$;
   $R_1$ is —CH(OH)CH$_2$C(=O)CH(CH$_3$)$_2$;
   $R_1$ is —CH(OH)CH$_2$CH$_2$C(CH$_3$)$_2$OH;
   $R_1$ is —CH(OH)CH$_2$C(=O)H;
   $R_1$ is —CH(OH)CH$_2$C(=O)OH;
   $R_1$ is —CH(OH)CH$_2$CH=CH—Ar (wherein Ar is aryl or heteroaryl);
   $R_1$ is —CH(OH)CH$_2$CH=CR'R" (wherein R' and R" are each independently hydrogen, alkyl, alkenyl, alkynyl, cycloalkyl, heteroalicyclic, aryl, or heteroaryl);
   $R_1$ is —NHAr (wherein Ar is aryl or heteroaryl);
   $R_1$ is —NHR (wherein R is hydrogen, alkyl, alkenyl, alkynyl, cycloalkyl, or heteroalicyclic);
   $R_1$ is —NHCH$_2$Ar (wherein Ar is aryl or heteroaryl);
   $R_1$ is —N(R')C(=O)OR" (wherein R' and R" are each independently hydrogen, alkyl, alkenyl, alkynyl, cycloalkyl, heteroalicyclic, aryl, or heteroaryl);
   $R_1$ is —N(R')C(=O)R" (wherein R' and R" are each independently hydrogen, alkyl, alkenyl, alkynyl, cycloalkyl, heteroalicyclic, aryl, or heteroaryl);
   $R_1$ is —N(R')C(=O)NR"R'" (wherein R', R" and R'" are each independently hydrogen, alkyl, alkenyl, alkynyl, cycloalkyl, heteroalicyclic, aryl, or heteroaryl);
   $R_1$ is —SR (wherein R is hydrogen, alkyl, alkenyl, alkynyl, cycloalkyl, or heteroalicyclic);
   $R_1$ is —SAr (wherein Ar is aryl or heteroaryl);
   $R_1$ is —SCH$_2$Ar (wherein Ar is aryl or heteroaryl);
   $R_1$ is —S(=O)R (wherein R is hydrogen, alkyl, alkenyl, alkynyl, cycloalkyl, heteroalicyclic, aryl, or heteroaryl);
   $R_1$ is —S(=O)$_2$R (wherein R is hydrogen, alkyl, alkenyl, alkynyl, cycloalkyl, heteroalicyclic, aryl, or heteroaryl);
   $R_1$ is hydrogen, alkyl, alkenyl, alkynyl, cycloalkyl, heteroalicyclic, aryl, or heteroaryl;
   $R_1$ is —CH(—OC(=O)NH$_2$)CH$_2$CH=CH(CH$_3$)$_2$;
   $R_1$ is —CH(—OC(=O)NHC(=O)CH$_3$)CH$_2$CH=CH(CH$_3$)$_2$;
   $R_1$ is —CH(—OC(=O)NHC(=O)CH$_2$Cl)CH$_2$CH=CH(CH$_3$)$_2$;
   $R_1$ is —CH(—OC(=O)R)CH$_2$CH=CH(CH$_3$)$_2$(wherein R is hydrogen, alkyl, alkenyl, alkynyl, cycloalkyl, heteroalicyclic, aryl, or heteroaryl);
   $R_1$ is —CH(—OC(=O)NHR)CH$_2$CH=CH(CH$_3$)$_2$ (wherein R is hydrogen, alkyl, alkenyl, alkynyl, cycloalkyl, or heteroalicyclic);
   $R_1$ is —CH(—OC(=O)NHAr)CH$_2$CH=CH(CH$_3$)$_2$ (wherein Ar is aryl or heteroaryl);
   $R_1$ is —O—Ar (wherein Ar is aryl or heteroaryl);
   $R_1$ is —OR (wherein R is hydrogen, alkyl, alkenyl, alkynyl, cycloalkyl, or heteroalicyclic);
   $R_1$ is —OCH$_2$Ar (wherein Ar is aryl or heteroaryl);
   $R_1$ is —CH(OR")R' (wherein R' and R" are each independently hydrogen, alkyl, alkenyl, alkynyl, cycloalkyl, heteroalicyclic, aryl, or heteroaryl),
b) compounds of Formula I, in which $R_1$ is —CH(OH)CH$_2$CH=C(CH$_3$)$_2$, $R_3$ and $R_6$ are each OH, and:
   $R_2$ is halo or hydroxy, and $R_4$ and $R_5$ are each hydrogen;
   $R_4$ is halo or hydroxy, and $R_2$ and $R_5$ are each hydrogen; and
   $R_5$ is halo or hydroxy, and $R_2$ and $R_4$ are each hydrogen,
c) compounds of Formula I, in which $R_3$ and $R_6$ are each alkoxy, and $R_2$, $R_4$ and $R_5$ are each hydrogen, and:
   $R_1$ is —CH(OR')R" (wherein R' and R" are each independently hydrogen, alkyl, alkenyl, alkynyl, cycloalkyl, heteroalicyclic, aryl, or heteroaryl);
   $R_1$ is —CH(OH)R (wherein R is hydrogen, alkyl, alkenyl, alkynyl, cycloalkyl, heteroalicyclic, aryl, or heteroaryl); and
   $R_1$ is —CHR'—OC(=O)OR" (wherein R' and R" are each independently hydrogen, alkyl, alkenyl, alkynyl, cycloalkyl, heteroalicyclic, aryl, or heteroaryl, provided that R" is not hydrogen),
d) compounds of Formula I, in which $R_3$ and $R_6$ are each alkoxy, $R_1$, $R_2$ and $R_4$ are each hydrogen, and:
   $R_5$ is —CH(OR")R' (wherein R' and R" are each independently hydrogen, alkyl, alkenyl, alkynyl, cycloalkyl, heteroalicyclic, aryl, or heteroaryl); and
   $R_5$ is —CH(OH)CH$_2$CH$_2$CH(CH$_3$)$_2$,
e) compounds of Formula I, in which $R_3$ and $R_6$ are each alkoxy, $R_2$, $R_4$ and $R_5$ are each hydrogen, and:
   $R_1$ is —CH(OR")R' (wherein R' and R" are each independently hydrogen, alkyl, alkenyl, alkynyl, cycloalkyl, heteroalicyclic, aryl, or heteroaryl); and
   $R_1$ is —CHR'—OC(=O)OR" (wherein R' and R" are each independently hydrogen, alkyl, alkenyl, alkynyl, cycloalkyl, heteroalicyclic, aryl, or heteroaryl, with the proviso that R" is not hydrogen),
f) compounds of Formula I, in which $R_2$ is methyl, $R_3$–$R_6$ are each hydrogen, and $R_1$ is:
   —CH$_2$CH=C(CH$_3$)CH$_2$CH$_2$CH$_2$CH(CH$_3$)CH$_2$CH$_2$CH$_2$CH(CH$_3$)CH$_2$CH$_2$CH$_2$CH(CH$_3$)$_2$; or
   —CH$_2$CH=C(CH$_3$)CH$_2$CH$_2$CH=C(CH$_3$)CH$_2$CH$_2$CH=C(CH$_3$)CH$_2$CH$_2$CH=C(CH$_3$)$_2$, and
g) compounds depicted in FIG. 1A or FIG. 1B.

Without being bound by any particular theory, it is believed that many commercially available preparations of shikonin comprise shikonin derivatives having one or more compound having a molecular weight as described herein. It is further believed that administration of such derivatives may provide a therapeutic effect similar to or even greater than shikonin per se (optionally by functioning as a prodrug of shikonin (e.g., decomposing in the body to form shikonin and a free saccharide), via enhancement of water solubility of shikonin by saccharide moieties, and or by providing a better fit to the active site with the active site of 3CL protease (e.g., wherein each of the three hydroxy groups of shikonin is substituted by a saccharide).

Shikonin and related compounds (according to any of the respective embodiments described herein) may optionally be derived from a plant of the borage family (Boraginaceae), optionally of the subfamily Boraginoideae, and optionally of the tribe Lithospermeae.

Examples of borage family species which may optionally be used as sources of shikonin or a related compound according to embodiments of the invention (according to any of the respective embodiments described herein) include, without limitation, species of the genera Lithospermum (e.g., *Lithospermum erythrorhizon*), Lithidora, Onosma (e.g., *Onosma visianii, Onosma heterophylla, Onosma panicolatum, Onosma echioides*), Echium (e.g., *Echium plantagineum*), Arnebia (e.g., *Arnebia hispidissima, Arnebia euchroma, Arnebia tibetana, Arnebia guttata*), and Alkanna (e.g., *Alkanna tinctoria*).

The naphthoquinone compound (e.g., shikonin or a derivative thereof) according to any of the respective embodiment may optionally be produced using plant tissue cultures (e.g., hairy root cultures), for example, using procedures such as described by Chaudhury & Pal [*J Crop Sci Biotech* 2010 13:99-106] and/or Sim & Chang [*Biotechnol Lett* 1993, 15:145-150].

The naphthoquinone compound (e.g., shikonin or a derivative thereof) according to any of the embodiments described herein may optionally be in a form of a product (e.g., a plant extract) which comprises the compound, e.g., along with additional components, including a wide variety of compounds found, extracted and/or isolated from a plant.

For example, the naphthoquinone compound (e.g., shikonin or a derivative thereof) according to any of the embodiments described herein may optionally be part of a plant extract (e.g., an ethanol and/or water extract), which may contain, for example, from about 0.5% to about 50% by weight of the naphthoquinone compound, and optionally from about 5% to about 40%, and optionally about 30% by weight. In some embodiments, at least a portion of the naphthoquinone compound (e.g., shikonin or a derivative thereof) in the plant extract is in a form of glycoside and/or a dimer or trimer thereof (according to any of the respective embodiments described herein). Shikonin and/or derivatives thereof may optionally be in a form of a composition (e.g., plant extract) described as "zicao", "zi cao", "ying zi cao", *Arnebia* or a variant thereof (e.g., "*Radix Arnebia*" or "*Arnebia euchroma*"), "purple gromwell", "red gromwell", "jichi", "murasaki", or variants thereof; and alkannin and/or derivatives thereof may optionally be in a form of a composition described as "alkanet extract" or "C. I. Natural Red 20".

The naphthoquinone compound (e.g., shikonin or a derivative thereof) according to any of the embodiments described herein may optionally be provided as a relatively pure preparation (e.g., at least 90% purity, or at least 95% purity). Such a relatively pure preparation may optionally be combined with a composition with a lower concentration of the active compound (e.g., a plant extract according to any of the respective embodiments described herein) in order to enhance the concentration of active compound in the plant extract (e.g., when a plant extract is considerably less costly than a relatively pure preparation).

In some of any of the embodiments described herein relating to a shikonin derivative, the shikonin derivative is a naphthoquinone compound found, extracted and/or isolated from a plant source, e.g., a plant source according to any of the respective embodiments described herein.

The naphthoquinone compound (e.g., shikonin or a derivative thereof) according to any of the embodiments described herein may also be prepared synthetically, using procedures known in the chemical arts.

Indications and Uses:

The compound of Formula I according to any of the respective embodiments described herein (e.g., in the respective section hereinabove) is optionally for use in the treatment of a viral infection, for example, a coronavirus infection.

According to an aspect of the embodiments of the invention, there is provided a use of a compound of Formula I according to any of the respective embodiments described herein (e.g., in the respective section hereinabove) in the manufacture of a medicament for use in the treatment of a viral infection, for example, a coronavirus infection.

According to an aspect of the embodiments of the invention, there is provided a method of treating a viral infection (for example, a coronavirus infection) in a (human or non-human) subject in need thereof, the method comprising administering to the subject a compound of Formula I according to any of the respective embodiments described herein (e.g., in the respective section hereinabove).

In some of any of the embodiments relating to treatment (according to any of the aspects described herein), the treatment is of a subject in which inhibiting inflammation would be beneficial, for example, in a subject considered to be afflicted by an excessive inflammatory response, which is deleterious, e.g., to the quality of life and/or chance of survival of the subject.

In some of any of the embodiments relating to treatment, the treatment comprises administration of the compound (according to any of the respective embodiments described herein) at least once per day, and optionally at least twice per day. In some such embodiments, administration is from 2 to 6 times per day, optionally 2, 3 or 4 times per day.

In some of any of the embodiments relating to treatment, the treatment comprises oral administration of the compound (according to any of the respective embodiments described herein), for example, wherein oral administration of the compound is effected at least 3 times per day, optionally four times per day.

In some of any of the respective embodiments, oral administration is at a dose in a range of from 10 mg to 5 grams, optionally from 50 mg to 1.5 gram, optionally from 150 mg to 500 mg, and optionally about 200 mg.

In some of any of the respective embodiments, oral administration is at a dosage in a range of from 2 mg per kg per day to 200 mg per kg per day, optionally in a range of from 5 mg per kg per day to 100 mg per kg per day, and optionally about 20 mg per kg per day.

In some of any of the embodiments relating to treatment, the treatment comprises intravenous administration of the compound (according to any of the respective embodiments described herein), for example, at a dose in a range of from 0.04 mg to 400 mg, optionally from 0.4 mg to 40 mg, and optionally about 4 mg.

In some of any of the embodiments relating to treatment, different dosages are used for different degrees of treatment urgency, for example, wherein a relatively low dosage (e.g., comprising administration twice per day of a relatively low amount of the compound, such as in a plant extract) is used as a prophylactic (e.g., following a known exposure to the virus, and/or during an epidemic in which future exposure to a virus has a relatively high probability); an intermediate dosage (e.g., comprising administration 3 times per day, optionally of a plant extract) is used to treat mild infections; and a relatively high dosage (e.g., comprising administration of a relatively high amount of the compound) is used to treat moderate and severe infections, for example, characterized by pneumonia.

In some of any of the embodiments relating to treatment, the naphthoquinone compound exhibits an antiviral activity, for example, an ability to inhibit proliferation of a virus in the subject's body. In some such embodiments, the naphthoquinone compound inhibits a protease (e.g., 3CL protease, or a corresponding virus which is essential for viral reproduction) of the virus (e.g., as determined using an assay for protease activity such as described in the Examples section herein). In some embodiments, the naphthoquinone compound inhibits autophagy (e.g., thereby inhibiting proliferation of a virus which utilizes autophagy to proliferate). In some embodiments, the naphthoquinone compound both inhibits a protease (e.g., 3CL protease) of the virus and inhibits autophagy.

Herein, the term "autophagy" refers to a natural process within cells whereby intracellular components are engulfed by vesicles (referred to as "autophagosomes") which can deliver the engulfed components to lysosomes to be degraded, or are directly engulfed by lysosomes.

In some of any of the embodiments relating to treatment, the naphthoquinone compound exhibits an anti-inflammatory effect, for example, an ability to reduce an inflammatory response in a subject's body (e.g., as determined by C-reactive protein levels, interleukin 17 (IL-17) and/or interleukin 6 (IL-6) levels). The anti-inflammatory effect is not a result of the antiviral effect, that is, is not dependent on first reducing a viral load in a subject. However, an anti-inflammatory effect may optionally cause an antiviral effect, for example, wherein the virus utilizes an inflammatory effect to facilitate proliferation (e.g., by escaping infected cells and/or entering cells upon damage of cells by the immune system). In some embodiments, the naphthoquinone compound exhibits an anti-inflammatory effect (according to any of the respective embodiments described herein), as well as an antiviral effect (according to any of the respective embodiments described herein), such as protease inhibition and/or autophagy inhibition.

Without being bound by any particular theory, it is believed that an anti-inflammatory effect is particularly useful in treating some viral infections (e.g., COVID-19), wherein much of the danger to a subject is associated with excessive inflammatory response, e.g., conditions associated with a cytokine storm. It is further believed that an anti-inflammatory effect and antiviral effect may act in synergy in treating a subject. For example, slower viral replication due to an antiviral effect may be effective at reducing a risk of cytokine storm even if it is not sufficiently potent to eliminate the virus.

Successful treatment outcomes include, without limitation, reduction in inflammation (e.g., as indicated by C-reactive protein levels), reduction in D-dimer levels (e.g., as an indicator of a reduction in over-coagulation), decrease in time until cure (as indicated by a negative result in a test for infection, e.g., by RT-PCR assay), decrease of hospitalization time, time until clinical improvement (e.g., as defined by a National Early Warning Score 2 (NEWS2) of ≤2 maintained for 24 hours), and/or the subject reporting an improvement in feeling (e.g., relative to placebo). Additional optional parameters for assessing sickness/health include, e.g., changes in blood pressure, heart rate, respiratory rate, saturation and/or body temperature; number of deaths in a group; incidence of deterioration and need of mechanical ventilation; and/or incidence and/or duration of time on supplemental oxygen.

Successful prophylactic treatment outcomes include, without limitation, avoidance of infection (in an individual), reduction of infection rate (in a population), and reduction or elimination of symptoms in infected individuals (e.g., wherein infection is indicated by production of antibodies against the virus).

In some of any of the embodiments described herein relating to treatment, the treatment comprises administering at least one additional active agent, in addition to administration of the naphthoquinone compound (e.g., according to any of the respective embodiments described herein). Administration of the additional active agent(s) may optionally be concomitant with or prior to or subsequent to administration of the naphthoquinone compound. In some embodiments, administration of the additional active agent(s) is effected at least twice per day, or at least three times per day, or at least four times per day, optionally four times per day.

The at least one additional active agent may be, for example, a vitamin, N-acetyl cysteine, an anticoagulant, an anti-inflammatory agent, an antipyretic agent, an antiviral agent, and/or a protease inhibitor.

The protease inhibitor may be, for example, any protease inhibitor described U.S. Patent Publication No. 2004/0198716, which is incorporated herein by reference, particularly a protease inhibitor described therein which is not a naphthoquinone compound as described herein. 5-methoxychromone is an example of such a protease inhibitor.

Examples of suitable vitamins include, without limitation, vitamin D (e.g., vitamin $D_3$) and vitamin C, optionally in a liposomal formulation.

Examples of suitable anticoagulants include, without limitation, rivaroxaban, nafamostat, omega 3 fatty acids (and lipids comprising them), heparin and derivatives thereof (e.g., enoxaparin sodium or fondaparinux), epoprostenol, clopidogrel, argatroban and curcumin.

Examples of suitable anti-inflammatory agents include, without limitation, ABX464; apremilast; atlizumab; baricitinib; berberine; cannabinoids, such as cannabidiol; celastrol; colchicine; curcuminoids, such as curcumin; decitabine; deferoxamine; DNase, such as dornase alfa; duvelisib; estradiol; elastase inhibitors, such as N-acetyl cysteine (NAC), freselestat, sivelestat, and/or any other compound depicted in FIG. 3; flavonoids (including substituted flavonoids, such as glycosides), such as quercetin and glycosides thereof (e.g., quercitrin, hyperoside, isoquercitrin and/or rutin), deoxykaempferol and glycosides thereof, and/or epigallocatechin gallate; infliximab; opioids, such as tramadol; palmitoylethanolamide (PEA); plant extracts, such as Boswellia extract and henna (*Lawsonia inermis*) extract; polyphenols, such as ellagic acid; stilbenoids, such as resveratrol and/or O-trimethyl-resveratrol); VB-201; NSAIDs (non-steroidal anti-inflammatory agents) such as aspirin, salicylate, salsalate, diflunisal, ibuprofen, naproxen, fenoprofen, ketoprofen, flurbiprofen, oxaprozin, loxoprofen, indomethacin, sulindac, etodolac, diclofenac, aceclofenac, tolmetin, ketorolac, nabumetone, piroxicam, meloxicam, tenoxicam, droxicam, lornoxicam, isoxicam mefenamic acid, meclofenamic acid, flufenamic acid, tolfenamic acid, celecoxib, rofecoxib, valdecoxib, parecoxib, lumiracoxib, etoricoxib, nimesulide, niflumic acid, licofenac, and/or clonixin; and/or glucocorticoids, such as alclometasone and prodrugs thereof (e.g., alclometasone dipropionate), amcinonide, beclometasone and esters thereof (e.g., beclometasone dipropionate), betamethasone, budesonide, ciclesonide, chloroprednisone and esters thereof (e.g., chloroprednisone 21-acetate), clobetasol and esters thereof (e.g., clobetasol propionate), clobetasone, clocortolone and esters thereof (e.g., clocortolone pivalate), cloprednol, cortisol (a.k.a. hydrocortisone), cortisone, cortivazol, deflazacort, desonide, desoximetasone, dexamethasone, diflucortolone and esters thereof (e.g., diflucortolone valerate), diflorasone and esters thereof (e.g., diflorasone diacetate), difluprednate, fluclorolone and prodrugs thereof (e.g., fluclorolone acetonide), fludroxycortide, flumetasone and esters thereof (e.g., flumetasone pivalate), flunisolide, fluocinolone and prodrugs thereof (e.g., fluocinolone acetonide), fluocinonide, fluocortin, fluocortolone, fluperolone and esters thereof (e.g., fluperolone acetate), fluprednidene and esters thereof (e.g., fluprednidene acetate), fluticasone and esters thereof (e.g., flutocasone furoate and fluticasone propionate), formocortal, halometasone, halcinonide, loteprednol, meprednisone, methylprednisolone, mometasone and esters thereof (e.g., mometasone furoate), paramethasone, prednisolone, prednisone, prednylidene, rimexolone, RU-28362, tixocortol and esters thereof (e.g., tixocortol pivalate), triamcinolone and prodrugs thereof (e.g., triamcinolone acetonide), and/or ulobetasol and esters thereof (e.g., ulobetasol propionate).

Examples of suitable antipyretic agents include, without limitation, NSAIDs (such as listed herein), paracetamol, and dipyrone.

Examples of suitable antiviral agents (e.g., 3CLpro inhibitors) include, without limitation, bamlanivimab, casirivimab, chloroquine, clevudine, coronavir, DIFF-1 (2-hexanoyl-4,6-dichloro-5-methoxyresorcinol), favipiravir, ivermectin, GC376, hydroxychloroquine, imdevimab, lopinavir, nalidixic acid, nitazoxanide, remdesivir, ritonavir, rupintrivir, tenofovir and/or TMC-310911.

Additionally, the additional active agent may optionally be any agent described for use in a clinical trial at the website www(dot)clinicaltrials(dot)gov/ct2/results?cond=COVID-19 as downloaded on Feb. 14, 2021, which is incorporated herein by reference in its entirety, especially with respect to agents for treating a coronavirus infection.

In some of any of the respective embodiments, N-acetyl cysteine is administered at a dosage in a range of from 0.2 to 6.4 grams per day, and optionally from 0.8 to 1.6 grams per day.

According to some of any of the embodiments described herein for any of the compositions, methods and uses described herein, the naphthoquinone compound as defined herein (e.g., a compound of Formula I) is used in combination with a vitamin (e.g., vitamin D or vitamin C, as described herein). In some such embodiments, the naphthoquinone compound is further used with N-acetyl cysteine, an anticoagulant, an anti-inflammatory agent, an antipyretic agent, an antiviral agent, and/or a protease inhibitor (e.g., according to any of the respective embodiments described herein).

According to some of any of the embodiments described herein for any of the compositions, methods and uses described herein, the naphthoquinone compound as defined herein (e.g., a compound of Formula I) is used in combination with an anticoagulant (e.g., an anticoagulant according to any of the respective embodiments described herein). In some such embodiments, the naphthoquinone compound is further used with a vitamin, N-acetyl cysteine, an anti-inflammatory agent, an antipyretic agent, an antiviral agent, and/or a protease inhibitor (e.g., according to any of the respective embodiments described herein).

According to some of any of the embodiments described herein for any of the compositions, methods and uses described herein, the naphthoquinone compound as defined herein (e.g., a compound of Formula I) is used in combination with an anti-inflammatory agent (e.g., an anti-inflammatory agent according to any of the respective embodiments described herein). In some such embodiments, the naphthoquinone compound is further used with a vitamin, N-acetyl cysteine, an anticoagulant, an antipyretic agent, an antiviral agent, and/or a protease inhibitor (e.g., according to any of the respective embodiments described herein).

According to some of any of the embodiments described herein for any of the compositions, methods and uses described herein, the naphthoquinone compound as defined herein (e.g., a compound of Formula I) is used in combination with an antipyretic agent (e.g., an antipyretic agent according to any of the respective embodiments described herein). In some such embodiments, the naphthoquinone compound is further used with a vitamin, N-acetyl cysteine, an anticoagulant, an anti-inflammatory agent, an antiviral agent, and/or a protease inhibitor (e.g., according to any of the respective embodiments described herein).

According to some of any of the embodiments described herein for any of the compositions, methods and uses described herein, the naphthoquinone compound as defined herein (e.g., a compound of Formula I) is used in combination with an antiviral agent (e.g., an antiviral agent according to any of the respective embodiments described herein). In some such embodiments, the naphthoquinone compound is further used with a vitamin, N-acetyl cysteine, an anticoagulant, an anti-inflammatory agent, an antipyretic agent, and/or a protease inhibitor (e.g., according to any of the respective embodiments described herein).

According to some of any of the embodiments described herein for any of the compositions, methods and uses described herein, the naphthoquinone compound as defined herein (e.g., a compound of Formula I) is used in combination with a protease inhibitor (e.g., a protease inhibitor according to any of the respective embodiments described herein). In some such embodiments, the naphthoquinone compound is further used with a vitamin, N-acetyl cysteine, an anticoagulant, an anti-inflammatory agent, an antipyretic agent, and/or an antiviral agent (e.g., according to any of the respective embodiments described herein).

According to an aspect of some embodiments, there is provided a method of inhibiting a coronavirus 3CL protease, the method comprising contacting the 3CL protease with a compound of Formula I according to any of the respective embodiments described herein (e.g., in the respective section hereinabove).

The method of inhibiting a coronavirus 3CL protease may optionally be effected in vitro and/or in vivo, in human or non-human subject (e.g., a mammal). In some embodiments, the method comprises administering the compound (according to any of the respective embodiments described herein) to a subject in need thereof (e.g., according to any of the embodiments described herein relating to subjects, treatment regimens and/or indications).

When the 3CL activity is inhibited in a subject, the method according to this aspect optionally further comprises inhibiting inflammation and/or autophagy in the subject (according to any of the respective embodiments described herein).

According to an aspect of some embodiments, there is provided a method of treating a coronavirus infection in a subject in need thereof, the method comprising administering to the subject at least one compound that exhibits at least two of (and optionally each of) the following properties:
(i) inhibition of an activity of a 3CL protease of the coronavirus;
(ii) inhibition of inflammation in the subject (optionally comprising reduction and/or prevention of a cytokine storm by inhibition of a kinase, such as Janus kinase (JAK); and
(iii) inhibition of autophagy in the subject.

The at least one compound may optionally comprise a single compound which exhibits the at least two properties described herein; or comprise a plurality of compounds which exhibits the at least two properties described herein; and/or comprise compounds which exhibit different properties, e.g., such that the at least two properties are exhibited by the combination of compounds but not by an individual compound.

The at least one compound according to this aspect optionally, but not necessarily, comprises a compound according to Formula I according to any of the respective embodiments described herein. In some embodiments, the treatment comprises administering, in addition to the compound according to Formula I, at least one additional agent that exhibits the abovementioned inhibition of activity of 3CL protease, inhibition of inflammation, and/or inhibition of autophagy, optionally supplementing one or two inhibitory activities which in the compound of Formula I is either weak or absent.

In some embodiments, the treatment comprises administering, in addition to the compound according to Formula I, at least one additional agent that exhibits the abovementioned inhibition of activity of 3CL protease, and optionally also inhibition of inflammation, and/or inhibition of autophagy.

In some embodiments, the treatment comprises administering, in addition to the compound according to Formula I, at least one additional agent that exhibits the abovementioned inhibition of inflammation, and optionally also inhibition of activity of 3CL protease and/or inhibition of autophagy.

In some embodiments, the treatment comprises administering, in addition to the compound according to Formula I, at least one additional agent that exhibits the abovementioned inhibition of autophagy, and optionally also inhibition of activity of 3CL protease and/or inhibition of inflammation.

The coronavirus according to any of the respective embodiments described herein is optionally a betacoronavirus, for example, an embecovirus (a.k.a. lineage A), sarbecovirus (a.k.a. lineage B), merbecovirus (a.k.a. lineage C), nobecovirus (a.k.a. lineage D), and hibecovirus. Exemplary betacoronaviruses include SARS-related coronavirus (a species of sarbecovirus), human coronavirus OC43, and human coronavirus HKU1, including any strains thereof (e.g., SARS-CoV-2).

Alternatively or additionally, the coronavirus may optionally be associated with the common cold, such as 229E, NL63, HKU1 and OC43 coronaviruses.

In some embodiments, the viral infection treatable using a naphthoquinone compound described herein is associated with a virus other than a coronavirus, for example, CMV (cytomegalovirus), HRV (human rhinoviruses), hepatovirus A, HMV (human meningo virus), and/or HIV (human immunodeficiency virus).

Pharmaceutical Compositions:

For any use and/or indication described herein, the naphthoquinone compound and/or additional active agent(s) of some embodiments of the invention can be administered to an organism per se, or in a form of a pharmaceutical composition, which may optionally further comprise suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to one or more agent accountable for the biological effect(s), for example, the naphthoquinone compound and/or additional active agent(s) according to any of the respective embodiments described herein. In some of any of the embodiments relating to a composition, the composition comprises one or more naphthoquinone compound (according to any of the respective embodiments described herein) and one or more additional active agent (according to any of the respective embodiments described herein).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

In some embodiments of any of the embodiments described herein, the naphthoquinone compound and/or additional active agent(s) (according to any of the respective embodiments described herein), are co-formulated in a single pharmaceutical composition.

Alternatively, in some embodiments of any of the embodiments described herein, each of the naphthoquinone compound and/or additional active agent(s) (according to any of the respective embodiments described herein) is formulated individually in a pharmaceutical composition. The composition comprising the naphthoquinone compound may optionally be co-administered with one or more composition comprising an additional active agent(s).

The naphthoquinone compound may be present in a composition at essentially any concentration, for example, from 0.01% to 99.99% by weight, optionally, from 0.1% to 50% by weight.

In some embodiments of any of the respective embodiments described herein, the composition comprising the naphthoquinone compound further comprises phospholipids. The weight ratio of phospholipids to the naphthoquinone compound in the composition is optionally in a range of from 10:1 to 1:10, and optionally from 3:1 to 1:3. In some exemplary embodiments, the phospholipid to naphthoquinone weight ratio is about 1:1.

The phospholipids (according to any of the respective embodiments described herein) are optionally composed primarily of phosphatidylcholine, that is, at least 50% (by weight) of the phospholipids are phosphatidylcholine. Optionally, at least 60% or at least 70% or at least 80% or at least 90% of the phospholipids are phosphatidylcholine (by weight).

The phospholipids (according to any of the respective embodiments described herein) optionally comprise phosphatidylserine, for example, such that at least 10% or at least 20% by weight of the phospholipids is phosphatidylserine. In some exemplary embodiments, the proportion of the phosphatidylserine in the phospholipids is about 20% by weight. In some of any of the aforementioned embodiments, the phospholipids are optionally composed primarily of phosphatidylcholine (according to any of the respective embodiments described herein).

Without being bound by any particular theory, it is believed that phospholipids (e.g., in an amount described herein) facilitate absorption of active ingredients into the blood (e.g., upon oral administration).

In some embodiments of any of the respective embodiments described herein, the composition further comprises liposomes, which optionally envelop at least a portion of the active ingredient(s). The liposomes may optionally comprise phospholipids (e.g., according to any of the respective embodiments described herein), for example, in combination with an aqueous carrier.

Alternatively, the composition may optionally be a dry composition, which forms liposomes upon contact with water.

Techniques for formulation and administration of drugs (according to any of the aspects of embodiments of the invention described herein) may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

In some embodiments of any of the embodiments described herein, administration of a naphthoquinone compound and/or additional active agent(s) is systemic.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups (e.g., for administration to children, optionally as a prophylactic treatment for healthy individuals), slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinylpyrrolidone, carbopol gel, polyethylene glycol, titanium dioxide, lacquer solutions and suitable organic solvents or solvent mixtures. Dyestuffs or pigments may be added to the tablets or dragee coatings for identification, or to characterize different combinations of active compound doses.

Pharmaceutical compositions that can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethylcellulose, sorbitol or dextran. Optionally, the suspension may also contain suitable stabilizers or agents that increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (naphthoquinone compound and/or additional active agent(s) described herein) effective to prevent, alleviate or ameliorate symptoms of a disorder (e.g., coronavirus infection) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed herein.

Additional Definitions:

As used herein throughout, the term "alkyl" refers to any saturated aliphatic hydrocarbon including straight chain and branched chain groups. Preferably, the alkyl group has 1 to 20 carbon atoms. Whenever a numerical range; e.g., "1 to 20", is stated herein, it implies that the group, in this case the hydrocarbon, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

Herein, the term "alkenyl" describes an unsaturated aliphatic hydrocarbon comprise at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 6 carbon atoms. The alkenyl group may be substituted or non-substituted. Substituted alkenyl may have one or more substituents, whereby each substituent group can independently be, for example, alkynyl, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino.

Herein, the term "alkynyl" describes an unsaturated aliphatic hydrocarbon comprise at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino.

A "cycloalkyl" group refers to a saturated on unsaturated all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein. When a cycloalkyl group is unsaturated, it may comprise at least one carbon-carbon double bond and/or at least one carbon-carbon triple bond.

An "aryl" group refers to an all-carbon monocyclic or fused-ring polycyclic (i.e., rings which share adjacent pairs of carbon atoms) having a completely conjugated pi-electron system. Examples, without limitation, of aryl groups are phenyl, naphthalenyl and anthracenyl. The aryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

A "heteroaryl" group refers to a monocyclic or fused ring (i.e., rings which share an adjacent pair of atoms) having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein. Representative examples are piperidine, piperazine, tetrahydrofuran, tetrahydropyran, morpholine and the like.

Herein, the terms "amine" and "amino" each refer to either a —NR'R" group or a —N$^+$R'R"R'" group, wherein R', R" and R'" are each hydrogen or a substituted or non-substituted alkyl, alkenyl, alkynyl, cycloalkyl, heteroalicyclic (linked to amine nitrogen via a ring carbon thereof), aryl, or heteroaryl (linked to amine nitrogen via a ring carbon thereof), as defined herein. Optionally, R', R" and R'" are hydrogen or alkyl comprising 1 to 4 carbon atoms. Optionally, R' and R" (and R'", if present) are hydrogen. When substituted, the carbon atom of an R', R" or R'" hydrocarbon moiety which is bound to the nitrogen atom of the amine is not substituted by oxo (unless explicitly indicated otherwise), such that R', R" and R'" are not (for example) carbonyl, C-carboxy or amide, as these groups are defined herein.

An "azide" group refers to a —N=N$^+$=N$^-$ group.

An "alkoxy" group refers to any of an —O-alkyl, —O-alkenyl, —O-alkynyl, —O-cycloalkyl, and —O-heteroalicyclic group, as defined herein.

An "aryloxy" group refers to both an —O-aryl and an —O-heteroaryl group, as defined herein.

A "hydroxy" group refers to a —OH group.

A "thiohydroxy" or "thiol" group refers to a —SH group.

A "thioalkoxy" group refers to any of an —S-alkyl, —S-alkenyl, —S-alkynyl, —S-cycloalkyl, and —S-heteroalicyclic group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' group, where R' is as defined herein.

An "O-carboxy" group refers to an R'C(=O)—O— group, where R' is as defined herein.

A "carboxylic acid" group refers to a —C(=O)OH group.

An "oxo" group refers to a =O group.

An "imine" group refers to a =N—R' group, where R' is as defined herein.

An "oxime" group refers to a =N—OH group.

A "hydrazone" group refers to a =N—NR'R" group, where each of R' and R" is as defined herein.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR"— group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

An "S-thiocarbamyl" group refers to an —SC(=O)—NR'R" group, where each of R' and R" is as defined herein.

An "amide" or "amido" group encompasses C-amido and N-amido groups, as defined herein.

A "C-amido" group refers to a —C(=O)—NR'R" group, where each of R' and R" is as defined herein.

An "N-amido" group refers to an R'C(=O)—NR"— group, where each of R' and R" is as defined herein.

A "urea group" refers to an —N(R')—C(=O)—NR"R'" group, where each of R', R" and R'" is as defined herein.

A "thiourea group" refers to a —N(R')—C(=S)—NR"R'" group, where each of R', R" and R'" is as defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

The term "hydrazine" describes a —NR'—NR"R'" group, with R', R", and R'" as defined herein.

As used herein, the term "hydrazide" describes a —C(=O)—NR'—NR"R'" group, where R', R" and R'" are as defined herein.

As used herein, the term "thiohydrazide" describes a —C(=S)—NR'—NR"R'" group, where R', R" and R'" are as defined herein.

A "guanidinyl" group refers to an —RaNC(=NRd)—NRbRc group, where each of Ra, Rb, Rc and Rd can be as defined herein for R' and R".

A "guanyl" or "guanine" group refers to an RaRbNC(=NRd)— group, where Ra, Rb and Rd are as defined herein.

For any of the embodiments described herein, the compound described herein may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt and/or a base addition salt.

An acid addition salt comprises at least one basic (e.g., amine and/or guanidinyl) group of the compound which is in a positively charged form (e.g., wherein the basic group is protonated), in combination with at least one counter-ion, derived from the selected acid, that forms a pharmaceutically acceptable salt. The acid addition salts of the compounds described herein may therefore be complexes formed between one or more basic groups of the compound and one or more equivalents of an acid.

A base addition salt comprises at least one acidic (e.g., carboxylic acid) group of the compound which is in a negatively charged form (e.g., wherein the acidic group is deprotonated), in combination with at least one counter-ion, derived from the selected base, that forms a pharmaceutically acceptable salt. The base addition salts of the compounds described herein may therefore be complexes formed between one or more acidic groups of the compound and one or more equivalents of a base.

Depending on the stoichiometric proportions between the charged group(s) in the compound and the counter-ion in the salt, the acid additions salts and/or base addition salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof, and/or a carboxylate anion and a base addition salt thereof.

The base addition salts may include a cation counter-ion such as sodium, potassium, ammonium, calcium, magnesium and the like, that forms a pharmaceutically acceptable salt.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

As used herein, the term "prodrug" refers to a compound which is converted in the body to an active compound (e.g., the compound of the formula described hereinabove). A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally ($C_{1-4}$)acyl (e.g., acetyl) group to form an ester group, and/or any one or more of the carboxylic acid groups of the compound is modified by an alkoxy or aryloxy group, optionally ($C_{1-4}$)alkoxy (e.g., methyl, ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The compounds described herein can be used as polymorphs and the present embodiments further encompass any isomorph of the compounds and any combination thereof.

As used herein the term "about" refers to ±20% or ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

As a general procedure, shikonin or a composition comprising shikonin or a derivative thereof is formulated in capsules, optionally in combination with lecithin (phospholipids, comprising primarily phosphatidylcholine) (e.g., at a shikonin-to-lecithin weight ratio of about 1:1). The shikonin or derivative thereof may be substantially pure (from a synthetic or natural source) or a part of an extract of a plant, such as *Lithospermum erythrorhizon, Arnebia euchroma* or another member of the borage family.

Using the above general procedure, an extract of purple gromwell (*Lithospermum erythrorhizon*) root (zicao) was prepared using an appropriate solvent, followed by spray drying and sieving, to obtain a purple powder. 175 mg of the powdered purple gromwell extract, containing about 30% shikonin and/or derivatives thereof, was placed with an equal weight of lecithin (Lipoid® PS P 20×, obtained from Lipoid GmbH) in Capsugel® delayed release (DR) capsules.

As an alternative to capsules, a syrup was prepared comprising lecithin and shikonin (95% purity) at a 5:1 lecithin: shikonin ratio, 44% alcohol as solvent, and honey.

Based on literature reports, toxicity of shikonin is not expected at dosages of less than 8 grams per day.

Example 2

Effect of Shikonin on 3CL Protease of SARS-Coronavirus 2 in an In Vitro Assay

Inhibition of the activity of 3CL protease of SARS-coronavirus 2 (the coronavirus associated with COVID-19) was determined by an assay based on commercial kit (BPS cat. 79955-1). 150 ng of 3CL protease was incubated with progressively smaller shikonin concentrations for 30 minutes. Shikonin was obtained from NLC pharma and was 95% pure. The reaction was initiated by addition of 50 μl of 50 μM kit substrate (25 μM final concentration), and then fluorescence was monitored (at 340 nm excitation wavelength, 510 nm emission wavelength) using a CLARIOstar® Plus plate reader (BMG Labtech). The 3CL protease activity was quantified as relative fluorescent units (RFU) per minute.

As shown in Table 1, the concentration at which shikonin inhibited 3CL protease by 50% (IC50) was about 10 μM, and almost complete inhibition of 3CL protease was exhibited at a concentration of 100 μM shikonin.

These results indicate that shikonin is capable of inhibiting SARS-coronavirus 2 3CL protease.

TABLE 1

Enzymatic activity of 3CL protease in presence of various concentrations of shikonin, as determined by fluorescent assay (mean ± standard deviation)

| Shikonin concentration | Activity (RFU/minute) |
|---|---|
| 100 μM | 2.9 ± 18.4 |
| 10 μM | 425.0 ± 7.8 |
| 1 μM | 680.1 ± 34.3 |
| 0.1 μM | 653.8 ± 28.1 |
| 0 μM | 743.7 ± 20.6 |

Example 3

Effect of purple gromwell extract on patients with COVID-19

The efficacy of an exemplary purple gromwell extract, prepared and formulated in capsules as described in Example 1, was evaluated in a clinical trial in patients afflicted by COVID-19. In one group, 10 patients received 175 mg of purple gromwell extract and lecithin, 4-8 times per day. In the other group, 19 patients received vitamin C and *spirulina* dietary supplement (control group). All patients were at an age in the range of 60-90 years.

In the group treated with purple gromwell extract, all 10 patients survived, 1 of the 10 (10%) needed artificial respiration, and the average time until release from the hospital was about 6-7 days. In contrast, in the other group, 5 patients (26%) died, 5 (26%) needed artificial respiration, and the average time until release from the hospital was about 3 weeks.

As shown in FIG. 2, patients treated with purple gromwell extract exhibited considerably lower levels of C-reactive protein (CRP) and ferritin (both of which are proteins associated with inflammation) than did control patients.

Indeed, in most cases, CRP levels of purple gromwell extract-treated patients normalized within several days, with typical levels of 4-20 mg/liter upon leaving the hospital.

High D-dimer levels were observed in six patients. One of the six was treated with purple gromwell extract and the D-dimer levels then returned to normal; whereas five received the control treatment, and none of the five survived.

These results indicate that purple gromwell extract is effective at treating viral diseases such as COVID-19 and reducing inflammation in a clinical setting.

In addition, the following case studies are presented:

Case 1: A 74 year-old male, with a history of bronchial asthma and COPD (being treated daily, including with oxygen), hypertension and diabetes mellitus, was prophylactically administered capsules containing purple gromwell extract daily for 6 months during the COVID-19 pandemic (with no other antiviral treatment). The subject was very socially active, in contact with many people. Two of the subject's assistants and his driver developed COVID-19 while working in his close presence, but the subject exhibited no signs of infection (including normal CPR test results).

Case 2: A 60 year-old male, with a history of ischemic heart disease, hypertension, excess weight, and appropriate treatments (including blood thinner injections), was diagnosed with COVID-19 (by PCR assay) following cough, weakness, and observation (by x-ray) of bilateral extended bronco-pneumonia. Following 24 hours of antibiotic and steroid treatment, his condition deteriorated and administration of vitamins and capsules containing purple gromwell extract began. About 48-72 hours later, the situation began to improve, and four days later, the shortness of breath and cough almost disappeared.

Case 3: A 68 year-old male, with no relevant medical history, was hospitalized with an oxygen saturation of 59%. COVID-19 and massive bilateral pneumonia were confirmed, and a treatment of antibiotics, steroids and blood thinner was initiated. His condition deteriorated (oxygen saturation of 10-20%) and he was intubated and put on an ICU-ventilator. Upon ventilation for 48 hours, no improvement was observed. A syrup (prepared as described in Example 1) comprising shikonin was then administered via a naso-gastric tube. At this stage, CRP levels were about 300. About 48-72 hours later, CRP levels dropped to 65, and a few days later reverted to normal. Shortly thereafter, oxygen saturation increased. The subject recovered and was released from the hospital 3 weeks later.

Case 4: An 81 year-old female, with a history of hypertension, diabetes mellitus and peripheral vascular disease (underwent brain catheterization), was diagnosed with COVID-19 (by PCR assay) after exhibiting progressively worsening shortness of breath. Treatment at home with oxygenation and steroids was initiated. The subject then developed fever and a cough, was diagnosed with pneumonia and began to receive antibiotics. After four days, the subject's health deteriorated further, leading to hospitalization. Oxygen saturation was 85%, and treatment with a respirator and remdesivir began. After five days, the condition was worse, with CRP levels of 120. The subject was then administered purple gromwell extract capsules and then attached to an ECMO unit. About 12 hours later, oxygen saturation stabilized at about 98%, and the following morning CRP levels decreased to 65. Four days later, the CRP levels decreased further to 15 and then decreased to normal; and clinical improvement was observed. The subject was released from the hospital 8-9 days after the initiation of the purple gromwell extract treatment.

Example 4

Preparation of Exemplary Capsule Formulation

RX-type capsules (capable of passing through the stomach and decomposing in the small intestines) are prepared with 200 mg of shikonin glycosides, as well as 200 mg of lecithin and a small amount of magnesium stearate (a lubricant). The shikonin glycosides comprise about 40% by weight monoglucosyl shikonin and about 60% by weight triglucosyl shikonin, and are relatively water-soluble.

Example 5

Preparation of Exemplary Capsule Formulation

Capsules are prepared with 250 mg of a root extract powder (prepared as described in Example 1 or obtained from a commercial source) and 250 mg lecithin with about 20% phosphatidylserine (Lipoid® PS P 20×, obtained from Lipoid GmbH). The root extract powder optionally comprises about 30% shikonin or derivative thereof by weight, such that the amount of active ingredient is about 75 mg.

Example 6

Preparation of Exemplary Capsule Formulation

Size 00 acid-resistant capsules (obtained from CapsCanada) are filled with a mixture of:
  135 mg microcrystalline cellulose (Avicel® PH102, obtained from DuPont Nutrition),
  100 mg lecithin with about 20% phosphatidylserine (Lipoid® PS P 20×, obtained from Lipoid GmbH),
  48 mg polyethylene glycol (PEG 3000, obtained from Merck),
  33 mg poloxamer 407 (Kolliphor® P407, obtained from BASF),
  120 mg shikonin (84.7% potency, obtained from Henan Steeda Industrial Co. Ltd.), and
  100 mg purple gromwell root extract powder (obtained from Imaherb).

The microcrystalline cellulose, shikonin, poloxamer and polyethylene glycol are ground, and then mixed with the lecithin and root extract powder, in suitable ratios. For example, 3752 grams of uniform mixture is used to fill 7000 capsules with 536 mg (±27 mg) of mixture per capsule.

The 120 mg shikonin of relatively high purity allows for a relatively high dose of shikonin, which is more difficult to obtain using only root extract powders. Such high-dose formulations are particularly suitable, for example, for treating moderate and severe cases of coronavirus infection.

Example 7

Effect of Exemplary Formulation on Patients with COVID-19

The efficacy of an exemplary shikonin-containing composition is assessed in a randomized, double-blind, placebo-controlled clinical study in hospitalized COVID-19 patients with SARS-CoV-2 infection confirmed (by RT-PCR assay). The administered composition is a liposomal formulation of shikonin prepared as described in Example 6.

Patients under the weight of 60 kg are administered 2 capsules, 3 times per day (6 capsules per day); patients within the weight range of 60-80 kg are administered 2 capsules, 4 times per day (8 capsules per day); and patients over the weight of 80 kg are administered 3 capsules, 4 times per day (12 capsules per day). Administration is during days 1-10 of the patient's hospitalization. Placebo capsules (comprising the same carrier without the active ingredients) are administered to an equally sized group of patients. Both groups receive standard of care for COVID-19 in addition to the capsules.

The effect of the shikonin-containing composition on sickness severity (relative to placebo) is assessed. Severity of sickness is evaluated as time until hospital discharge and/or time until clinical improvement as defined by a National Early Warning Score 2 (NEWS2) of ≤2 maintained for 24 hours.

Additional parameters for assessing sickness/health include, e.g., changes in blood pressure, heart rate, respiratory rate, saturation and/or body temperature; time from first day of treatment until negative test result (by RT-PCR assay) for virus; number of deaths in group; incidence of deterioration and need of mechanical ventilation; and/or incidence and/or duration of time on supplemental oxygen.

Example 8

Effect of *Arnebia euchroma* Extract on 3CL Protease of SARS-Coronavirus 2 in an In Vitro Assay Inhibition of the activity of recombinant 3CL protease of SARS-coronavirus 2 by *Arnebia euchroma* extract was determined. The extract was identified by the manufacturer as containing 30% shikonin, but appeared upon HPLC examination to contain shikonin only in the form of glycosides, e.g., at a molecular weight of about 800 Da.

A fluorescence assay was performed using 96-well black non-binding flat bottom plates (Greiner Bio-One), with a reaction volume of 100 µl. 50 µl of 150 ng 3CL protease was incubated with the extract in reaction buffer for 30 minutes at room temperature. A reaction was initiated by adding 50 µl solution of peptide substrate (1 µM) in reaction buffer (5 mM Bolt™, 50 mM Tris, pH 8.0, 0.75 M $Na_2SO_4$). The substrate was CBR1_488 or Covidyte™ TF670, which results in fluorescence at 488 nm or 670 nm, respectively, upon cleavage by 3CL protease. Fluorescence was monitored on Synergy™ HT plate reader (BioTek), with emission/excitation at 485/525 nm or 590/645 nm, respectively. The indicated concentrations are those of shikonin as reported by the manufacturer (i.e., assumes original extract contains 30% shikonin).

As shown in Table 2, the extract inhibited 3CL protease, with the $IC_{50}$ being between 1.25 and 2.5 µM for the assay with detection at 488 nm, and between 5 and 10 µM for the assay with detection at 670 nm.

TABLE 2

Enzymatic activity of SARS-COV-2 3CL protease in presence of various amounts of *Arnebia euchroma* extract, as determined by fluorescent assays at 488 and 670 nm (nominal shikonin concentration based on extract having 30% shikonin as reported by manufacturer)

| Nominal shikonin concentration | Activity (RFU/minute) | |
|---|---|---|
| | 488 nm assay | 670 nm assay |
| 20 μM | 16 | 137 |
| 10 μM | 27 | 153 |
| 5 μM | 55 | 259 |
| 2.5 μM | 125 | 315 |
| 1.25 μM | 345 | 398 |
| 0 μM | 604 | 419 |
| Blank | 15 | 18 |

These results indicate that *Arnebia euchroma* extract comprises shikonin derivatives which inhibit 3CL protease of SARS-CoV-2, and which may be even more potent than shikonin.

Example 9

Preparation of Exemplary Enteric Coated Tablet Formulations

Tablet cores were prepared as follows: 30 mg per tablet microcrystalline cellulose (Avicel® 101), 10 mg per tablet colloidal silicon dioxide (Aerosil® 200, obtained from Evonik), 250 mg per tablet phosphatidyl serine, and 275 mg per tablet shikonin at about 95% purity (obtained from Henan) were mixed by wet granulation, with the aid of 40 mg ethanol. 200 mg per tablet mannitol DC (obtained from Merck), 10 mg per tablet colloidal silicon dioxide (Aerosil® 200), 100 mg per tablet microcrystalline cellulose (Avicel® 102, obtained from Mingtai), 20 mg per tablet crospovidone (Kollidon® CL), and 10 mg per tablet magnesium stearate were then mixed by dry granulation. The tablet cores were formed by tablet press using a Dio/Punch set no. 3542× 7480/19.5×9 mm, oval standard, capsule shape.

Figure 4:
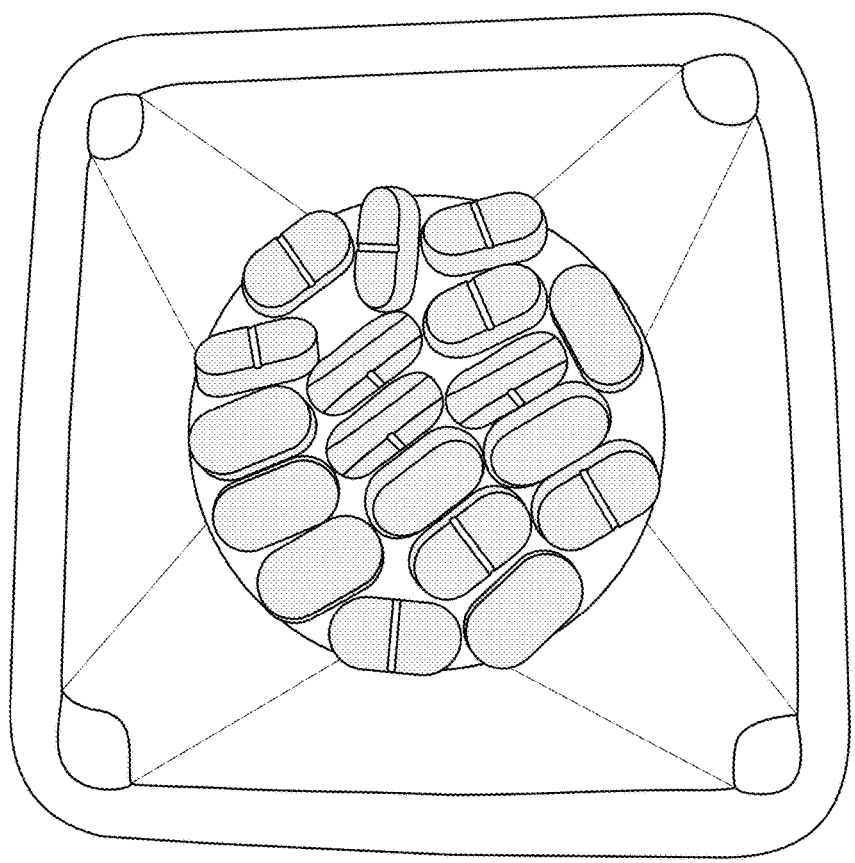
FIG. 4 presents a photograph of exemplary enteric-coated shikonin tablets according to some embodiments of the invention.

The tablet cores were then coated by a composition comprising 28 grams Eudragit® L100 enteric polymer, 5.6 grams triethyl citrate, 193.2 grams 1-propanol, 113.2 grams acetone, 1.5 gram Red Ponceau, to obtain red, smoothly coated tablets, as depicted in FIG. 4.

Additional tablets were prepared as described hereinabove, with the ingredients in the wet granulation and dry granulation stages being as described below in Table 3.

TABLE 3

Exemplary tablet core compositions

| Ingredients (mg per tablet) | | | |
|---|---|---|---|
| | Composition A | Composition B | Composition C |
| Wet granulation | | | |
| Microcrystalline cellulose (Avicel® 101) | 200 | 200 | 200 |
| 20% Phosphatidylserine | 100 | 100 | 100 |
| Phosphatidylcholine (Phospholipon® 90) | 78 | 78 | 78 |
| Shikonin (~95% purity) | 112 | 112 | 112 |
| Poloxamer 407 (Spectrum) | — | — | 45 |
| Colloidal SiO₂ (Aerosil® 200) | — | — | 20 |
| Vitamin E TPGS | — | 40 | — |
| Ethanol | 80 | 40 | 40 |
| Dry granulation | | | |
| Colloidal SiO₂ (Aerosil® 200) | 10 | 10 | 10 |
| Mannitol DC | 260 | 260 | 255 |
| Microcrystalline cellulose (Avicel® 102) | 100 | 100 | 100 |
| Crospovidone (Kollidon® CL) | 30 | 30 | 30 |
| Magnesium stearate | 10 | 10 | 10 |

The tablet cores were formed by tablet press using a Dio/Punch set no. 3543×6496/16×9 mm, oval standard, capsule shape.

The tablet cores were then coated by the coating composition described hereinabove.

Tablets (with about 250 mg shikonin) were analyzed by HPLC and UV spectroscopy and Dissolution apparatus II (USP). Tablets were exposed to simulated gastric fluid (pH 1.0-1.2, 0.1 N HCl) for 120 minutes, followed by simulated intestinal fluid (pH 6.8, 0.1 SLS in buffer) for 120 minutes.

Figure 5:
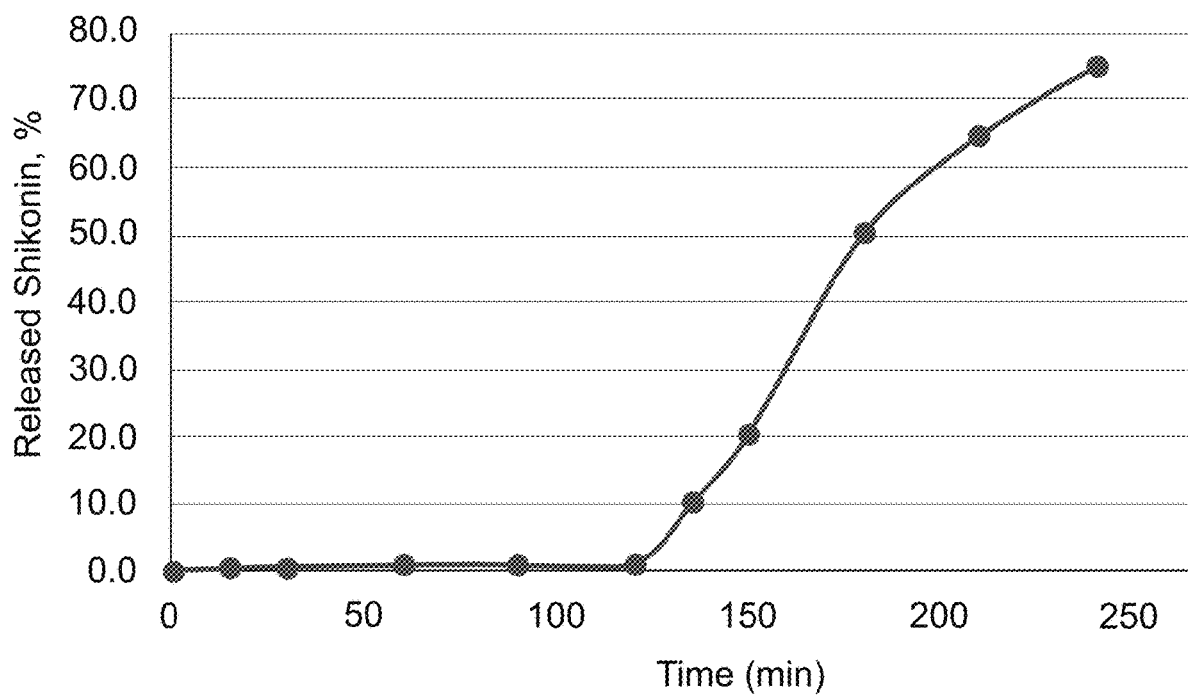
FIG. 5 presents a graph showing release of shikonin from exemplary enteric-coated shikonin tablets as a function of time, wherein the first 120 minutes is under simulated gastric conditions and the next 120 minutes are under simulated intestinal conditions.

As shown in FIG. 5, almost none of the shikonin was released under simulated gastric conditions over the course of 2 hours, whereas about 75% of the shikonin was released within 2 hours under simulated intestinal conditions.

The dissolution of tablets prepared with Compositions A, B and C (as described in Table 3) was analyzed as described hereinabove.

As shown in Table 4, tablets formed from each of Compositions A, B and C released almost of the shikonin therein upon exposure to simulated intestinal conditions, while releasing almost none of the shikonin under simulated gastric conditions. Tablets of Composition C (with about 5% poloxamer) dissolved particularly rapidly, whereas tablets of Compositions A and B dissolved more gradually.

TABLE 4

Percentage of shikonin released from exemplary tablets upon exposure for 2 hours to simulated gastric conditions (pH 1.0) followed by exposure for 6 hours to simulated intestinal conditions (pH 6.8)

| Time (hours) | pH | Composition A (% release) | Composition B (% release) | Composition C (% release) |
|---|---|---|---|---|
| 0 | 1.0 | 0.0 | 0.0 | 0.0 |
| 2 | 1.0 | 0.0 | 0.2 | 0.0 |
| 2.5 | 6.8 | 16.0 | 0.4 | 3.6 |
| 3 | 6.8 | 38.0 | 22.4 | 73.0 |
| 4 | 6.8 | 71.7 | 55.7 | 90.0 |
| 5 | 6.8 | 79.5 | 78.9 | 91.0 |
| 6 | 6.8 | 82.2 | 86.2 | 91.0 |
| 8 | 6.8 | 89.1 | 93.8 | 91.0 |

These results indicate that the tablets release shikonin in an effective and highly controlled manner, and that dissolution rate may be controlled using appropriate excipients, such as poloxamer.

Example 10

Preparation of Exemplary Capsule Formulations

Phospholipid-containing, phytosome-like compositions comprising a *Lithospermum erythrorhizon* extract were prepared as described in Table 5, and used to fill size 0 capsules (by semi-automatic capsule filling machine). Ingredients were mixed by wet granulation, and in some cases by dry granulation, as detailed in Table 5. The weight of the capsule content was selected for optimal flow of granules into the capsules.

TABLE 5

Exemplary capsule content compositions

| Ingredient | Ingredients (mg per capsule) and granulation technique (wet or dry) | | |
|---|---|---|---|
| | Composition I | Composition II | Composition III |
| Microcrystalline cellulose (Avicel ® 101) | 200 (wet) | 152 (wet) | 125 (wet) |
| 20% Phosphatidylserine | 100 (wet) | 100 (wet) | 100 (dry) |
| Phosphatidylcholine (Phospholipon ® 90) | 78 (wet) | 60 (wet) | 50 (wet) |
| Shikonin (~95% purity) | 107 (wet) | 115 (wet) | 130 (wet) |
| *L. erythrorhizon* extract | 100 (wet) | 100 (wet) | 100 (dry) |
| Poloxamer 407 (Spectrum) | 45 (wet) | 30 (wet) | 25 (wet) |
| Colloidal SiO$_2$ (Aerosil ® 200) | 20 (wet) | 20 (wet) | 20 (wet) |
| Ethanol | 40 | 100 | 80 |

The dissolution of capsules filled with Compositions I, II and III (as described in Table 5) were analyzed according to procedures such as described in Example 9.

As shown in Table 6, Composition I exhibited slow release (possibly associated with an effect of the plant extract), whereas Compositions II and III exhibited full release after about 1-2 hours in simulated intestinal conditions. No significant release was observed under simulated gastric conditions.

TABLE 6

Percentage of shikonin released from exemplary capsules upon exposure for 2 hours to simulated gastric conditions (pH 1.0) followed by exposure for 6 hours to simulated intestinal conditions (pH 6.8)

| Time (hours) | pH | Composition I (% release) | Composition II (% release) | Composition III (% release) |
|---|---|---|---|---|
| 0 | 1 | 0.0 | 0.0 | 0.0 |
| 2 | 1.0 | 2.0 | 2.3 | 3.5 |
| 2.5 | 6.8 | 19.3 | 31.0 | 62.1 |
| 3 | 6.8 | 28.0 | 64.9 | 93.1 |
| 4 | 6.8 | 37.2 | 91.4 | 102.4 |
| 5 | 6.8 | 38.8 | 91.3 | 102.9 |
| 6 | 6.8 | 39.3 | 91.5 | 102.7 |
| 8 | 6.8 | 89.1 | 93.8 | 91.0 |

These results indicate that capsules can release shikonin in an effective and highly controlled manner.

Example 11

Exemplary Formulations with Additional Active Agents

Figure 3:
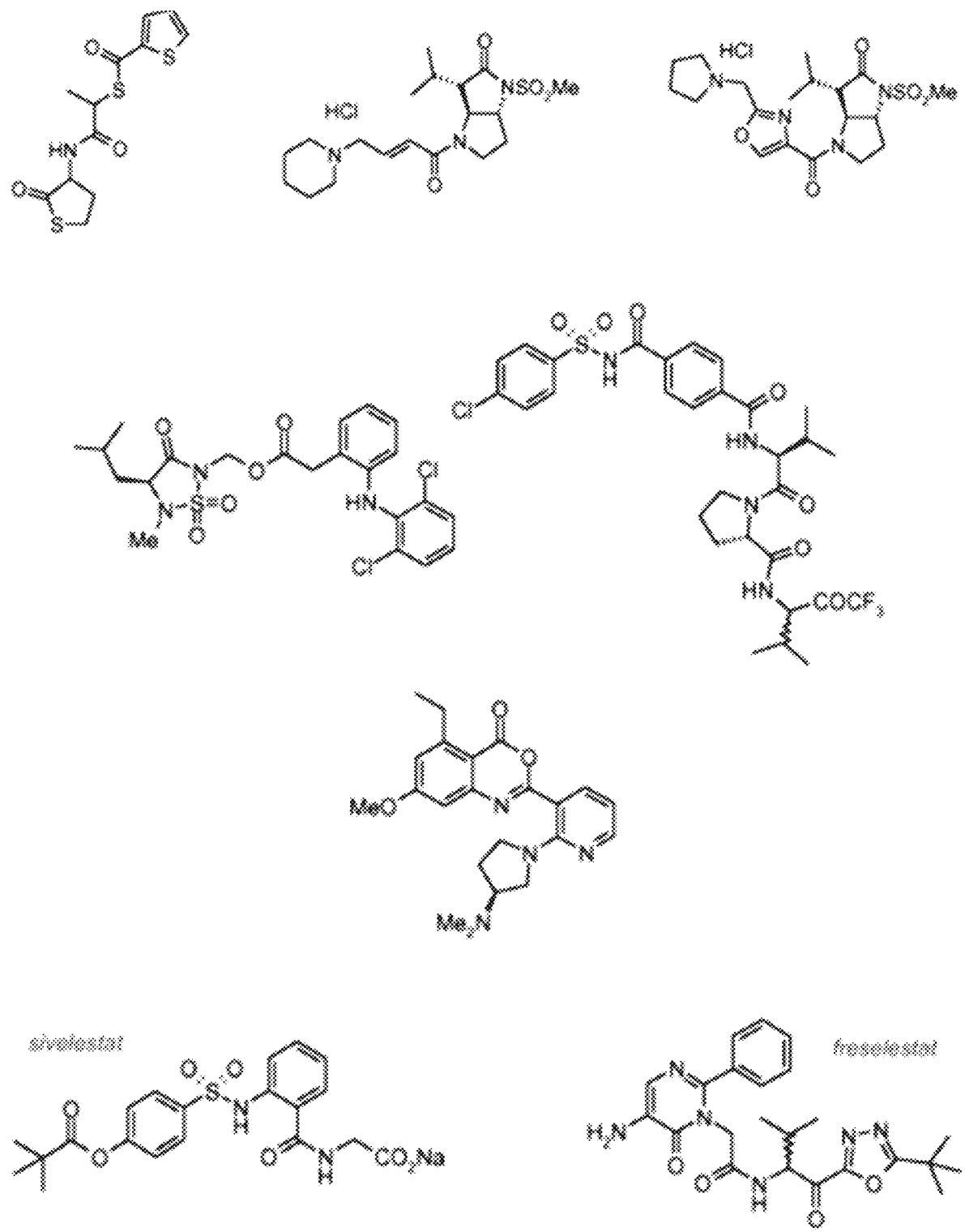
FIG. 3 depicts exemplary additional active agents which may be co-administered with a 3CL protease inhibitor according to some embodiments of the invention.

A composition is prepared according to procedures as described in any one of Example 1, 4, 5 and 6, except that the composition further includes at least one additional active agent with a 3C protease inhibitor activity (e.g., 2-hexanoyl-4,6-dichloro-5-methoxyresorcinol, a.k.a. "DIFF-1") and/or an anti-inflammatory activity, such as:

- an IL6 and/or IL17 inhibitor, optionally one or more flavonoid (e.g., deoxykaempferol or quercetin), substituted flavonoid (e.g., epigallocatechin gallate (EGCG) and/or quercitrin), stilbenoid (e.g., resveratrol and/or O-trimethyl-resveratrol), polyphenol (e.g., ellagic acid), curcuminoid (e.g., curcumin), berberine, celastrol, and/or plant extract (e.g., a Boswellia extract and/or henna (*Lawsonia inermis*) extract); and/or
- an elastase inhibitor, optionally N-acetylcysteine and/or one or more compounds depicted in FIG. 3.

The composition is optionally tested for activity in vitro (e.g., according to procedures described in Example 2 or 8); and/or in a clinical setting (e.g., according to procedures described in Example 3 or 7). The composition may be assessed for synergistic activity by comparison with the activity of naphthoquinone (e.g., shikonin of a derivative thereof) alone and the abovementioned additional active agent(s) without the naphthoquinone.

Alternatively, a composition as described in Example 1 is used in combination with one or more compositions that include one or more of the additional active agents described above.

The two or more compositions are tested for activity in vitro (e.g., according to procedures described in Example 2 or 8), by contacting the 3CL protease with the compositions, either simultaneously or sequentially; and/or in a clinical setting (e.g., according to procedures described in Example 3 or 7), by administering the two or more compositions to a patient either simultaneously or sequentially. The combination therapy may be assessed for synergistic activity by comparison with the activity of the naphthoquinone alone and the abovementioned additional active agent(s) without the naphthoquinone.

Example 12

Liposomal Formulations

Liposomes are prepared and loaded with shikonin or a derivative thereof (e.g., derived from a plant extract) according to any suitable technique known in the art. The amount of liposomes is optionally such that a weight of the liposome lipids (e.g., lecithin, phosphatidylcholine, phosphatidylserine and/or PEGylated lipids) is from 2% to 100% of the weight of the shikonin (or derivative thereof) in the composition (e.g., from 5 to 500 mg liposome lipids). The liposomal formulation optionally further comprises one or more additional active agents such as described in Example 8.

The liposomes are optionally formulated using procedures such as described hereinabove, e.g., by placing a liquid composition comprising liposomes in a capsule shell.

To form a "phytosome" formulation, phosphatidylcholine and/or phosphatidylserine and a plant extract described herein (which comprises shikonin or a derivative thereof) are optionally dissolved and mixed rigorously in ethanol, and then filtered, followed by solvent evaporation (e.g., at room temperature). The obtained solid is ground to granule size of less than 80 microns, and then homogenized.

The liposomal composition is optionally tested for activity in vitro (e.g., according to procedures described in Example 2 or 8); and/or in a clinical setting (e.g., according to procedures described in Example 3 or 7). The effect of the liposomes may be determined by comparison with the activity of a corresponding composition without liposomes.

Example 13

Compositions Comprising Additional Naphthoquinone Derivatives

A composition is prepared according to procedures described in Example 1, 4, 5, 6, 11 and/or 12, except that instead of (or in addition to) the active ingredient described hereinabove, a related compound, such as alkannin (e.g., purified alkannin from a synthetic or natural source, or alkannin which is part of an extract of a plant, such as *Alkanna tinctoria* another member of the borage family), deoxyshikonin or an ester (e.g., acetate, isobutyrate, isovalerate 2-methyl-butyrate, β-hydroxyisovalerate, or β,β-dimethylacrylate ester) of shikonin or alkannin is used.

The composition is optionally tested for activity in vitro (e.g., according to procedures described in Example 2 or 8); and/or in a clinical setting (e.g., according to procedures described in Example 3 or 7).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A pharmaceutical composition comprising:
    a compound represented by Formula I:

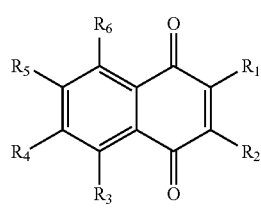

Formula I wherein $R_1$-$R_6$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, or alternatively, $R_1$ and $R_2$ together form a five- or six-membered aromatic or aliphatic ring, and further comprising:

a) at least one phospholipid, wherein a weight ratio of said at least one phospholipid to said compound in the composition is in a range of from 10:1 to 1:10, and/or b) liposomes.

2. The pharmaceutical composition of claim 1, comprising at least one phospholipid, wherein a weight ratio of said at least one phospholipid to said compound in the composition is in a range of from 10:1 to 1:10.

3. The pharmaceutical composition of claim 1, comprising liposomes.

4. The pharmaceutical composition of claim 1, wherein at least one, or each, of $R_3$ and $R_6$ is OH.

5. The pharmaceutical composition of claim 1, wherein $R_1$ is represented by:

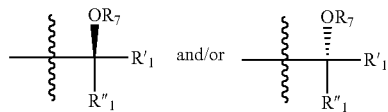

wherein $R'_1$, $R''_1$, and $R_7$ are each independently selected from the group consisting of hydrogen, alkyl, alkenyl, alkynyl, cycloalkyl, heteroalicyclic, and carbonyl.

6. The pharmaceutical composition of claim 5, wherein $R_7$ is a saccharide moiety or a peptide moiety, or wherein $R_7$ is hydrogen or carbonyl.

7. The pharmaceutical composition of claim 1, wherein the compound is shikonin or a glycoside of shikonin, or an ester thereof.

8. The pharmaceutical composition of claim 1, further comprising at least one additional active agent selected from the group consisting of a vitamin, N-acetyl cysteine, an anticoagulant, an anti-inflammatory agent, an antipyretic agent, an antiviral agent, and a protease inhibitor.

9. The pharmaceutical composition of claim 8, wherein said protease inhibitor is capable of inhibiting 3C protease and/or a 3CL protease.

10. The pharmaceutical composition of claim 1, capable of at least one of:
    (i) inhibiting an activity of a 3CL protease;
    (ii) inhibiting inflammation; and
    (iii) inhibiting autophagy.

* * * * *